(12) United States Patent
Messerli

(10) Patent No.: US 11,406,508 B2
(45) Date of Patent: Aug. 9, 2022

(54) FLEXIBLE ELONGATED CHAIN IMPLANT AND METHOD OF SUPPORTING BODY TISSUE WITH SAME

(71) Applicant: DePuy Synthes Products, Inc., Raynham, MA (US)

(72) Inventor: Dominique Messerli, Downingtown, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 15/801,335

(22) Filed: Nov. 2, 2017

(65) Prior Publication Data
US 2018/0049884 A1   Feb. 22, 2018

Related U.S. Application Data

(63) Continuation of application No. 15/333,275, filed on Oct. 25, 2016, now Pat. No. 9,956,085, which is a
(Continued)

(51) Int. Cl.
*A61F 2/44* (2006.01)
*A61B 17/70* (2006.01)
(Continued)

(52) U.S. Cl.
CPC .............. *A61F 2/441* (2013.01); *A61B 17/68* (2013.01); *A61B 17/7094* (2013.01); *A61F 2/44* (2013.01);
(Continued)

(58) Field of Classification Search
CPC ........................... A61F 2/44; A61F 2002/4415
(Continued)

(56) References Cited

U.S. PATENT DOCUMENTS

| 2,381,050 A | 8/1945 | Hardinge |
| 4,611,581 A | 9/1986 | Steffee |

(Continued)

FOREIGN PATENT DOCUMENTS

| DE | 197 10 392 C1 | 7/1999 |
| DE | 103 09 986 A1 | 9/2004 |

(Continued)

OTHER PUBLICATIONS

Cotten, Anne., MD., et al. "Percutaneous Vertebroplasty for Osteolytic Metastases and Myeloma: Effects of the Percentage of Lesion Filling and the Leakage of Methyl Methacrylate at Clinical Followup"., Radiology 1996; 200:525-530.
(Continued)

*Primary Examiner* — Matthew J Lawson
(74) *Attorney, Agent, or Firm* — Barnes & Thornburg LLP

(57) ABSTRACT

Implants and methods for augmentation, preferably by minimally invasive procedures and means, of body tissue, including in some embodiments repositioning of body tissue, for example, bone and, preferably vertebrae are described. The implant may comprise one or more chain linked bodies inserted into the interior of body tissue. As linked bodies are inserted into body tissue, they may fill a central portion thereof and for example in bone can push against the inner sides of the cortical exterior surface layer, for example the end plates of a vertebral body, thereby providing structural support and tending to restore the body tissue to its original or desired treatment height. A bone cement or other filler can be added to further augment and stabilize the body tissue. The preferred implant comprises a single flexible monolithic chain formed of allograft cortical bone having a plurality of substantially non-flexible bodies connected by substantially flexible links.

12 Claims, 8 Drawing Sheets

Related U.S. Application Data continuation of application No. 15/259,817, filed on Sep. 8, 2016, now abandoned, which is a continuation of application No. 15/040,217, filed on Feb. 10, 2016, now Pat. No. 10,881,520, which is a continuation of application No. 13/558,662, filed on Jul. 26, 2012, now Pat. No. 9,289,240, which is a continuation of application No. 11/633,131, filed on Dec. 1, 2006, now abandoned.

(60) Provisional application No. 60/810,453, filed on Jun. 2, 2006, provisional application No. 60/753,782, filed on Dec. 23, 2005.

(51) Int. Cl.
A61B 17/68 (2006.01)
A61B 17/00 (2006.01)
A61F 2/30 (2006.01)
A61F 2/36 (2006.01)

(52) U.S. Cl.
CPC .............. *A61F 2/442* (2013.01); *A61F 2/447* (2013.01); *A61F 2/4455* (2013.01); *A61F 2/4465* (2013.01); *A61B 2017/00004* (2013.01); *A61B 2017/00526* (2013.01); *A61F 2/3609* (2013.01); *A61F 2002/30593* (2013.01); *A61F 2002/4415* (2013.01); *A61F 2210/0004* (2013.01); *A61F 2250/0003* (2013.01)

(58) Field of Classification Search
USPC .......................................... 623/17.11–17.16
See application file for complete search history.

(56) References Cited

U.S. PATENT DOCUMENTS

| | | |
|---|---|---|
| 4,820,349 A | 4/1989 | Saab |
| 4,839,215 A | 6/1989 | Starling et al. |
| 4,863,476 A | 9/1989 | Shepperd |
| 4,969,888 A | 11/1990 | Scholten et al. |
| 5,041,114 A | 8/1991 | Chapman et al. |
| 5,053,049 A | 10/1991 | Campbell |
| 5,059,193 A | 10/1991 | Kuslich |
| 5,108,404 A | 4/1992 | Scholten et al. |
| 5,123,926 A | 6/1992 | Pisharodi |
| 5,298,254 A | 3/1994 | Prewett et al. |
| 5,370,611 A | 12/1994 | Niezink et al. |
| 5,370,661 A | 12/1994 | Branch |
| 5,374,267 A | 12/1994 | Siegal |
| 5,397,322 A | 3/1995 | Campopiano |
| 5,425,732 A | 6/1995 | Ulrich et al. |
| 5,522,894 A | 6/1996 | Draenert |
| 5,522,899 A | 6/1996 | Michelson |
| 5,534,023 A | 7/1996 | Henley |
| 5,549,679 A | 8/1996 | Kuslich |
| 5,637,042 A | 6/1997 | Breese |
| 5,665,122 A | 9/1997 | Kambin |
| 5,690,678 A | 11/1997 | Johnson |
| 5,693,100 A | 12/1997 | Pisharodi |
| 5,697,977 A | 12/1997 | Pisharodi |
| 5,702,454 A * | 12/1997 | Baumgartner .......... A61F 2/441 128/898 |
| 5,716,416 A | 2/1998 | Lin |
| 5,755,797 A | 5/1998 | Baumgartner |
| 5,756,127 A | 5/1998 | Grisoni et al. |
| 5,759,191 A | 6/1998 | Barbere |
| 5,782,831 A | 7/1998 | Sherman et al. |
| 5,827,289 A | 10/1998 | Reiley et al. |
| 5,843,189 A | 12/1998 | Perouse |
| 5,865,848 A | 2/1999 | Baker |
| 5,868,749 A * | 2/1999 | Reed .................... A61B 17/80 606/104 |
| 5,878,886 A | 3/1999 | Marshall |
| 5,899,939 A | 5/1999 | Boyce et al. |
| 5,919,235 A | 7/1999 | Husson et al. |
| 5,958,465 A | 9/1999 | Klemm et al. |
| 5,961,554 A | 10/1999 | Janson et al. |
| 5,972,015 A | 10/1999 | Scribner et al. |
| 5,976,186 A | 11/1999 | Bao et al. |
| 6,045,579 A | 4/2000 | Hochshuler et al. |
| 6,090,998 A | 7/2000 | Grooms et al. |
| 6,096,038 A | 8/2000 | Michelson |
| 6,126,689 A | 10/2000 | Brett |
| 6,127,597 A | 10/2000 | Beyar et al. |
| 6,149,651 A | 11/2000 | Drewry et al. |
| 6,162,231 A | 12/2000 | Mikus et al. |
| 6,176,882 B1 | 1/2001 | Biedermann et al. |
| 6,179,856 B1 | 1/2001 | Barbere |
| 6,183,768 B1 | 2/2001 | Harle |
| 6,189,537 B1 | 2/2001 | Wolfinbarger, Jr. |
| 6,206,923 B1 | 3/2001 | Boyd et al. |
| 6,235,043 B1 | 5/2001 | Reiley et al. |
| 6,241,734 B1 | 6/2001 | Scribner et al. |
| 6,248,110 B1 | 6/2001 | Reiley et al. |
| 6,277,120 B1 | 8/2001 | Lawson |
| 6,290,718 B1 | 9/2001 | Grooms et al. |
| 6,293,970 B1 | 9/2001 | Wolfinbarger, Jr. et al. |
| 6,305,379 B1 | 10/2001 | Wolfinbarger, Jr. |
| 6,325,802 B1 | 12/2001 | Frigg |
| 6,332,894 B1 | 12/2001 | Stalcup et al. |
| 6,340,477 B1 | 1/2002 | Anderson |
| 6,387,130 B1 | 5/2002 | Stone et al. |
| 6,413,278 B1 | 7/2002 | Marchosky |
| 6,419,676 B1 | 7/2002 | Zucherman et al. |
| 6,423,083 B2 | 7/2002 | Reiley et al. |
| 6,440,138 B1 | 8/2002 | Reiley et al. |
| 6,488,710 B2 | 12/2002 | Besselink |
| 6,491,714 B1 | 12/2002 | Bennett |
| 6,544,289 B2 | 4/2003 | Wolfinbarger, Jr. et al. |
| 6,576,016 B1 | 6/2003 | Hochshuler et al. |
| 6,595,998 B2 | 7/2003 | Johnson et al. |
| 6,602,291 B1 | 8/2003 | Ray et al. |
| 6,610,094 B2 | 8/2003 | Husson |
| 6,613,054 B2 | 9/2003 | Scribner et al. |
| 6,620,162 B2 | 9/2003 | Kuslich et al. |
| 6,632,235 B2 | 10/2003 | Weikel et al. |
| 6,648,891 B2 | 11/2003 | Kim |
| 6,652,592 B1 | 11/2003 | Grooms et al. |
| 6,652,593 B2 | 11/2003 | Boyer, II et al. |
| 6,663,647 B2 | 12/2003 | Reiley et al. |
| 6,679,886 B2 | 1/2004 | Weikel et al. |
| 6,706,069 B2 | 3/2004 | Berger |
| 6,719,761 B1 | 4/2004 | Reiley et al. |
| 6,733,535 B2 | 5/2004 | Michelson |
| 6,764,514 B1 | 7/2004 | Li et al. |
| 6,776,800 B2 | 8/2004 | Boyer, II et al. |
| 6,802,844 B2 | 10/2004 | Ferree |
| 6,805,713 B1 | 10/2004 | Carter et al. |
| 6,835,208 B2 | 12/2004 | Marchosky |
| 6,855,169 B2 | 2/2005 | Boyer, II et al. |
| 6,863,672 B2 | 3/2005 | Reiley et al. |
| 6,869,445 B1 | 3/2005 | Johnson |
| 6,899,719 B2 | 5/2005 | Reiley et al. |
| 6,913,621 B2 | 7/2005 | Boyd et al. |
| 6,969,404 B2 | 11/2005 | Ferree |
| 6,981,981 B2 | 1/2006 | Reiley et al. |
| 7,025,771 B2 | 4/2006 | Kuslich et al. |
| 7,044,954 B2 | 5/2006 | Reiley et al. |
| 7,060,066 B2 | 6/2006 | Zhao et al. |
| 7,097,648 B1 | 8/2006 | Globerman et al. |
| 7,153,307 B2 | 12/2006 | Scribner et al. |
| 7,166,121 B2 | 1/2007 | Reiley et al. |
| 7,179,299 B2 | 2/2007 | Edwards et al. |
| 7,220,282 B2 | 5/2007 | Kuslich |
| 7,226,475 B2 | 6/2007 | Lenz et al. |
| 7,226,481 B2 | 6/2007 | Kuslich |
| 7,238,209 B2 | 7/2007 | Matsuzaki et al. |
| 7,241,297 B2 | 7/2007 | Shaolian et al. |
| 7,241,303 B2 | 7/2007 | Reiss et al. |
| 7,261,720 B2 | 8/2007 | Stevens et al. |
| 7,326,248 B2 | 2/2008 | Michelson |

(56) References Cited

U.S. PATENT DOCUMENTS

| | | | |
|---|---|---|---|
| 7,341,601 B2 | 3/2008 | Eisermann et al. | |
| 7,351,262 B2 | 4/2008 | Bindseil et al. | |
| 7,427,295 B2 | 9/2008 | Ellman et al. | |
| 7,442,210 B2 | 10/2008 | Segal et al. | |
| 7,503,920 B2 | 3/2009 | Siegal | |
| 7,655,010 B2 | 2/2010 | Serhan et al. | |
| 7,666,226 B2 | 2/2010 | Schaller | |
| 7,670,374 B2 | 3/2010 | Schaller | |
| 7,703,727 B2 | 4/2010 | Selness | |
| 7,731,751 B2 | 6/2010 | Butler et al. | |
| 7,771,458 B2 | 8/2010 | Biedermann et al. | |
| 7,785,368 B2 | 8/2010 | Schaller | |
| 7,799,081 B2 | 9/2010 | McKinley | |
| 7,837,734 B2 | 11/2010 | Zucherman et al. | |
| 7,850,733 B2 | 12/2010 | Baynham et al. | |
| 7,918,874 B2 | 4/2011 | Siegal | |
| 7,942,903 B2 | 5/2011 | Moskowitz et al. | |
| 7,947,078 B2 | 5/2011 | Siegal | |
| 8,007,535 B2 | 8/2011 | Hudgins et al. | |
| 8,034,110 B2 | 10/2011 | Garner et al. | |
| 8,057,544 B2 | 11/2011 | Schaller | |
| 8,080,061 B2 | 12/2011 | Appenzeller et al. | |
| 8,105,382 B2 | 1/2012 | Olmos et al. | |
| 8,157,806 B2 | 4/2012 | Frigg et al. | |
| 8,206,423 B2 | 6/2012 | Siegal | |
| 8,236,029 B2 | 8/2012 | Siegal | |
| 8,241,328 B2 | 8/2012 | Siegal | |
| 8,246,622 B2 | 8/2012 | Siegal et al. | |
| 8,262,666 B2 | 9/2012 | Baynham et al. | |
| 8,267,939 B2 | 9/2012 | Cipoletti et al. | |
| 8,267,971 B2 | 9/2012 | Dutoit et al. | |
| 8,328,812 B2 | 12/2012 | Siegal et al. | |
| 8,343,193 B2 | 1/2013 | Johnson et al. | |
| 8,366,777 B2 | 2/2013 | Matthis et al. | |
| 8,403,990 B2 | 3/2013 | Dryer et al. | |
| 8,454,617 B2 | 6/2013 | Schaller et al. | |
| 8,465,524 B2 | 6/2013 | Siegal | |
| 8,486,109 B2 | 7/2013 | Siegal | |
| 8,579,981 B2 | 11/2013 | Lim et al. | |
| 8,597,330 B2 | 12/2013 | Siegal | |
| 8,663,294 B2 | 3/2014 | Dutoit et al. | |
| 8,672,977 B2 | 3/2014 | Siegal et al. | |
| 8,777,993 B2 | 7/2014 | Siegal et al. | |
| 8,845,638 B2 | 9/2014 | Siegal et al. | |
| 8,900,235 B2 | 12/2014 | Siegal | |
| 8,906,098 B2 | 12/2014 | Siegal | |
| 8,961,609 B2 | 2/2015 | Schaller | |
| 8,986,388 B2 | 3/2015 | Siegal et al. | |
| 9,017,408 B2 | 4/2015 | Siegal et al. | |
| 9,017,413 B2 | 4/2015 | Siegal et al. | |
| 9,044,334 B2 | 6/2015 | Siegal et al. | |
| 9,254,138 B2 | 2/2016 | Siegal et al. | |
| 9,283,092 B2 | 3/2016 | Siegal et al. | |
| 9,289,240 B2 | 3/2016 | Messerli | |
| 9,408,712 B2 | 8/2016 | Siegal et al. | |
| 9,956,085 B2 | 5/2018 | Messerli | |
| 2001/0001129 A1 | 5/2001 | McKay et al. | |
| 2001/0056302 A1* | 12/2001 | Boyer, II | B29C 43/006 623/17.15 |
| 2002/0029084 A1* | 3/2002 | Paul | A61F 2/28 623/23.63 |
| 2002/0049444 A1 | 4/2002 | Knox | |
| 2002/0068974 A1 | 6/2002 | Kuslich et al. | |
| 2002/0120346 A1* | 8/2002 | Boyer, II | A61B 17/0401 623/23.63 |
| 2002/0138133 A1 | 9/2002 | Lenz et al. | |
| 2002/0143328 A1 | 10/2002 | Shluzas et al. | |
| 2002/0156531 A1 | 10/2002 | Felt et al. | |
| 2002/0183752 A1 | 12/2002 | Steiner et al. | |
| 2003/0018390 A1 | 1/2003 | Husson | |
| 2003/0028251 A1 | 2/2003 | Mathews | |
| 2003/0060892 A1 | 3/2003 | Richter et al. | |
| 2003/0088249 A1 | 5/2003 | Fuerderer | |
| 2003/0135275 A1 | 7/2003 | Garcia et al. | |
| 2003/0139812 A1 | 7/2003 | Garcia et al. | |
| 2003/0199979 A1 | 10/2003 | McGuckin | |
| 2004/0002761 A1 | 1/2004 | Rogers et al. | |
| 2004/0010314 A1 | 1/2004 | Matsuzaki et al. | |
| 2004/0018128 A1 | 1/2004 | Gupta | |
| 2004/0049282 A1 | 3/2004 | Gjunter | |
| 2004/0059418 A1 | 3/2004 | McKay et al. | |
| 2004/0073308 A1 | 4/2004 | Kuslich et al. | |
| 2004/0078080 A1 | 4/2004 | Thramann et al. | |
| 2004/0087947 A1 | 5/2004 | Lim et al. | |
| 2004/0097930 A1 | 5/2004 | Justis et al. | |
| 2004/0102774 A1 | 5/2004 | Trieu | |
| 2004/0117019 A1 | 6/2004 | Trieu et al. | |
| 2004/0177847 A1 | 9/2004 | Foley et al. | |
| 2004/0204710 A1 | 10/2004 | Patel et al. | |
| 2004/0210226 A1 | 10/2004 | Trieu | |
| 2004/0210297 A1 | 10/2004 | Lin et al. | |
| 2004/0220615 A1 | 11/2004 | Lin et al. | |
| 2004/0225361 A1 | 11/2004 | Glenn et al. | |
| 2004/0230309 A1 | 11/2004 | DiMauro et al. | |
| 2004/0249463 A1 | 12/2004 | Bindseil et al. | |
| 2004/0249464 A1* | 12/2004 | Bindseil | A61F 2/4455 623/17.16 |
| 2005/0015148 A1 | 1/2005 | Jansen et al. | |
| 2005/0021040 A1 | 1/2005 | Bertagnoli | |
| 2005/0027358 A1 | 2/2005 | Suddaby | |
| 2005/0027366 A1 | 2/2005 | Saini et al. | |
| 2005/0070911 A1 | 3/2005 | Carrison et al. | |
| 2005/0090824 A1 | 4/2005 | Shluzas et al. | |
| 2005/0090901 A1 | 4/2005 | Studer | |
| 2005/0113855 A1 | 5/2005 | Kennedy et al. | |
| 2005/0119752 A1 | 6/2005 | Williams et al. | |
| 2005/0131548 A1 | 6/2005 | Boyer et al. | |
| 2005/0154463 A1 | 7/2005 | Trieu | |
| 2005/0192662 A1 | 9/2005 | Ward | |
| 2005/0203533 A1 | 9/2005 | Ferguson et al. | |
| 2005/0209595 A1 | 9/2005 | Karmon | |
| 2005/0209629 A1 | 9/2005 | Kerr et al. | |
| 2005/0209695 A1 | 9/2005 | de Vries et al. | |
| 2005/0234498 A1 | 10/2005 | Gronemeyer et al. | |
| 2005/0251259 A1 | 11/2005 | Suddaby | |
| 2005/0273167 A1 | 12/2005 | Triplett et al. | |
| 2005/0278023 A1 | 12/2005 | Zwirkoski | |
| 2006/0036241 A1 | 2/2006 | Siegal | |
| 2006/0036273 A1 | 2/2006 | Siegal | |
| 2006/0041258 A1 | 2/2006 | Galea | |
| 2006/0052874 A1 | 3/2006 | Johnson et al. | |
| 2006/0064172 A1 | 3/2006 | Trieu | |
| 2006/0079905 A1 | 4/2006 | Beyar et al. | |
| 2006/0089715 A1 | 4/2006 | Truckai et al. | |
| 2006/0095138 A1 | 5/2006 | Truckai et al. | |
| 2006/0100304 A1 | 5/2006 | Vresilovic et al. | |
| 2006/0100706 A1 | 5/2006 | Shadduck et al. | |
| 2006/0106459 A1 | 5/2006 | Truckai et al. | |
| 2006/0122625 A1 | 6/2006 | Truckai et al. | |
| 2006/0122701 A1 | 6/2006 | Kiester | |
| 2006/0129244 A1 | 6/2006 | Ensign | |
| 2006/0136064 A1 | 6/2006 | Sherman | |
| 2006/0142858 A1 | 6/2006 | Colleran et al. | |
| 2006/0149268 A1 | 7/2006 | Truckai et al. | |
| 2006/0149278 A1 | 7/2006 | Abdou | |
| 2006/0149379 A1 | 7/2006 | Kuslich et al. | |
| 2006/0189999 A1 | 8/2006 | Zwirkoski | |
| 2006/0235426 A1 | 10/2006 | Lim et al. | |
| 2006/0247781 A1 | 11/2006 | Francis | |
| 2006/0265077 A1 | 11/2006 | Zwirkoski | |
| 2006/0271061 A1 | 11/2006 | Beyar et al. | |
| 2006/0293750 A1 | 12/2006 | Sherman et al. | |
| 2007/0010889 A1 | 1/2007 | Francis | |
| 2007/0055266 A1 | 3/2007 | Osorio et al. | |
| 2007/0055267 A1 | 3/2007 | Osorio et al. | |
| 2007/0055272 A1 | 3/2007 | Schaller | |
| 2007/0055274 A1 | 3/2007 | Appenzeller et al. | |
| 2007/0055280 A1 | 3/2007 | Osorio et al. | |
| 2007/0055284 A1 | 3/2007 | Osorio et al. | |
| 2007/0055285 A1 | 3/2007 | Osorio et al. | |
| 2007/0093822 A1 | 4/2007 | Dutoit et al. | |
| 2007/0093846 A1 | 4/2007 | Frigg et al. | |
| 2007/0093899 A1 | 4/2007 | Dutoit et al. | |
| 2007/0093901 A1 | 4/2007 | Grotz et al. | |

(56) References Cited

U.S. PATENT DOCUMENTS

| | | |
|---|---|---|
| 2007/0093912 A1 | 4/2007 | Borden |
| 2007/0123986 A1 | 5/2007 | Schaller |
| 2007/0162132 A1 | 7/2007 | Messerli |
| 2007/0270955 A1 | 11/2007 | Chow |
| 2008/0065067 A1 | 3/2008 | Steinberg |
| 2008/0133012 A1 | 6/2008 | McGuckin |
| 2008/0161927 A1 | 7/2008 | Savage et al. |
| 2008/0221586 A1 | 9/2008 | Jarcia-Bengochea et al. |
| 2008/0234827 A1 | 9/2008 | Schaller et al. |
| 2008/0306595 A1 | 12/2008 | McLeod et al. |
| 2009/0216234 A1 | 8/2009 | Farr et al. |
| 2010/0076502 A1 | 3/2010 | Guyer et al. |
| 2010/0145392 A1 | 6/2010 | Dutoit et al. |
| 2011/0029083 A1 | 2/2011 | Hynes et al. |
| 2011/0029085 A1 | 2/2011 | Hynes et al. |
| 2011/0125266 A1 | 5/2011 | Rodgers et al. |
| 2012/0290096 A1 | 11/2012 | Messerli |
| 2012/0310352 A1 | 12/2012 | DiMauro et al. |
| 2012/0310355 A1 | 12/2012 | Dutoit et al. |
| 2013/0190875 A1 | 7/2013 | Shulock et al. |
| 2014/0052259 A1 | 2/2014 | Garner et al. |
| 2016/0199107 A1 | 7/2016 | Messerli |
| 2016/0374818 A1 | 12/2016 | Messerli |
| 2017/0035573 A1 | 2/2017 | Messerli |

FOREIGN PATENT DOCUMENTS

| | | |
|---|---|---|
| EP | 0 493 789 A1 | 7/1992 |
| EP | 0 621 020 A1 | 10/1994 |
| EP | 1 308 134 A3 | 7/2003 |
| FR | 2 287 894 A1 | 5/1976 |
| JP | 06-154258 A | 6/1994 |
| JP | 2001-516618 A | 10/2001 |
| JP | 2003-126108 A | 5/2003 |
| JP | 2004-508889 A | 3/2004 |
| JP | 2005-510258 A | 4/2005 |
| JP | 2005-537098 A | 12/2005 |
| WO | 92/02184 A1 | 2/1992 |
| WO | 93/13723 A1 | 7/1993 |
| WO | 99/13805 A1 | 3/1999 |
| WO | 00/74605 A1 | 12/2000 |
| WO | 01/54598 A1 | 8/2001 |
| WO | 02/24122 A2 | 3/2002 |
| WO | 02/64180 A1 | 8/2002 |
| WO | 03/099171 A1 | 12/2003 |
| WO | 2004/019815 A2 | 3/2004 |
| WO | 2004/047689 A1 | 6/2004 |
| WO | 2004/086934 A2 | 10/2004 |
| WO | 2004/108019 A2 | 12/2004 |
| WO | 2005/009299 A1 | 2/2005 |
| WO | 2005/027734 A2 | 3/2005 |
| WO | 2005/041796 A1 | 5/2005 |
| WO | 2005/092248 A1 | 10/2005 |
| WO | 2005/094735 A2 | 10/2005 |
| WO | 2007/038349 A2 | 4/2007 |
| WO | 2007/076049 A2 | 7/2007 |
| WO | 2009/006432 A2 | 1/2009 |
| WO | 2010/075555 A2 | 7/2010 |
| WO | 2012/027490 A2 | 3/2012 |

OTHER PUBLICATIONS

Cotten, Anne, et al., "Preoperative Percutaneous Injection of Methyl Methacrylate and N-Butyl Cyanoacrylate in Vertebral Hemangiomas"; AJNR 17:137-142 (1996).

Fürderer et al., "Vertebral body stenting," Orthopade 31:356-361 (2002) (in German, with English language translation).

Gaitanis et al., "Balloon kyphoplasty for the treatment of pathological vertebral compression fractures," Eur Spine J 14:250-260 (2005).

Gangi, Afshin, et al., "Percutaneous Vertebroplasty Guided by a Combination of CT and Fluoroscopy"., AJNR 15:83-86, Jan. 1994.

International Search Report and Written Opinion for Application No. PCT/US2006/024009 dated Feb. 7, 2007 (13 pages).

International Preliminary Report on Patentability for Application No. PCT/US2006/024009 dated Dec. 24, 2007 (10 pages).

International Search Report and Written Opinion for Application No. PCT/US2006/037119 dated Jun. 12, 2009 (14 pages).

International Preliminary Report on Patentability for Application No. PCT/US2006/037119 dated Jun. 16, 2009 (10 pages).

International Search Report and Written Opinion for Application No. PCT/US2006/040083 dated Mar. 1, 2007 (10 pages).

International Preliminary Report on Patentability for Application No. PCT/US2006/040083 dated Apr. 16, 2008 (8 pages).

International Search Report and Written Opinion for Application No. PCT/2006/046822 dated Aug. 7, 2007 (13 pages).

International Preliminary Report on Patentability for Application No. PCT/US2006/046822 dated Jun. 11, 2008 (9 pages).

International Search Report and Written Opinion for Application No. PCT/US2006/049105 dated Nov. 6, 2007 (13 pages).

International Preliminary Report on Patentability for Application No. PCT/US2006/049105 dated Jun. 24, 2008 (8 pages).

Jang, "Pulmonary embolism of polymethylmethacrylate after percutaneous vertebroplasty: a report of three cases," Spine 27(19):E416-E418 (2002).

Jensen, Mary E., et al., "Percutaneous Polymethylmethacrylate Vertebroplasty in the Treatment of Osteoporotic Vertebral Body Compression Fractures: Technical Aspects"., AJNR: vol. 18, pp. 1897-1904, Nov. 1997.

Lieberman et al., "Initial outcome and efficacy of kyphoplasty in the treatment of painful osteoporotic vertebral compression fractures," Spine 26(14): 1631-1638 (2001).

Maciunas, Robert J., MD., "Endovascular Neurological Intervention"; American Association of Neurological Surgeons; 153-158, 1995.

Magerl et al., "A comprehensive classification of thoracic and lumbar injuries," Eur Spine J, 3, 184-201 (1994).

Truumees, "Comparing kyphoplasty and vertebroplasty," Advances in Osteoporotic Fracture Management 1(4), 114-123 (2002).

* cited by examiner

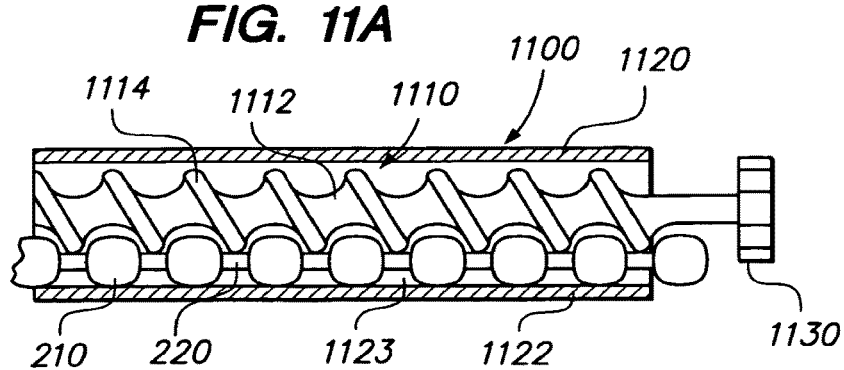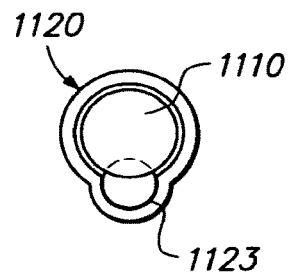
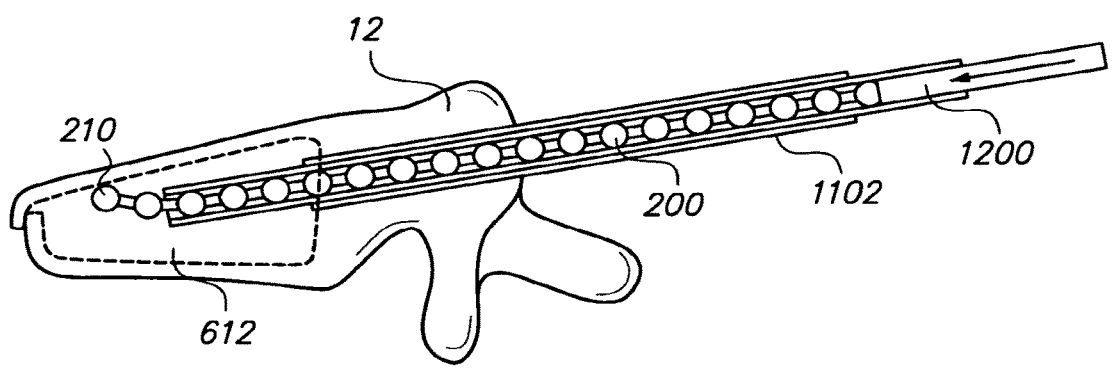
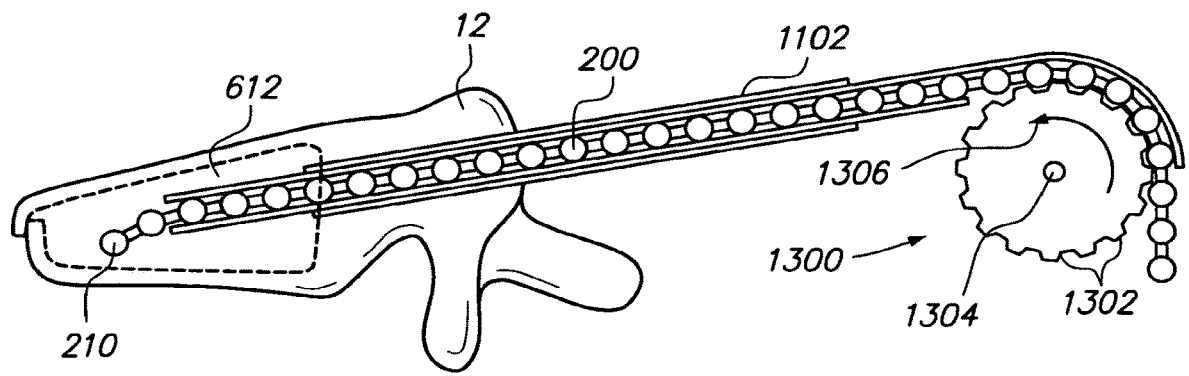

FLEXIBLE ELONGATED CHAIN IMPLANT AND METHOD OF SUPPORTING BODY TISSUE WITH SAME

CROSS-REFERENCE TO RELATED APPLICATIONS

This application is a continuation of U.S. patent application Ser. No. 15/333,275, filed Oct. 25, 2016, which is a continuation of U.S. patent application Ser. No. 15/259,817, filed Sep. 8, 2016, which is a continuation of U.S. patent application Ser. No. 15/040,217, filed Feb. 10, 2016, which is a continuation of U.S. patent application Ser. No. 13/558,662, filed Jul. 26, 2012 (now U.S. Pat. No. 9,289,240), which is a continuation of U.S. patent application Ser. No. 11/633,131, filed Dec. 1, 2006 (now abandoned), which claims priority to U.S. Provisional Patent Application No. 60/753,782, filed Dec. 23, 2005 and U.S. Provisional Patent Application No. 60/810,453, filed Jun. 2, 2006, the entirety of each of which is incorporated by reference herein.

FIELD OF THE INVENTION

The invention relates to implants, and more particularly to flexible chain implants for augmenting or supporting bones or other structures, such as, for example vertebral discs.

BACKGROUND OF THE INVENTION

Vertebral compression fractures, as illustrated in FIG. 1, represent a generally common spinal injury and may result in prolonged disability. These fractures involve collapsing of one or more vertebral bodies 12 in the spine 10. Compression fractures of the spine usually occur in the lower vertebrae of the thoracic spine or the upper vertebra of the lumbar spine. They generally involve fracture of the anterior portion 18 of the affected vertebra 12 (as opposed to the posterior side 16). Spinal compression fractures can result in deformation of the normal alignment or curvature, e.g., lordosis, of vertebral bodies in the affected area of the spine. Spinal compression fractures and/or related spinal deformities can result, for example, from metastatic diseases of the spine, from trauma or can be associated with osteoporosis. Until recently, doctors were limited in how they could treat such compression fractures and related deformities. Pain medications, bed rest, bracing or invasive spinal surgery were the only options available.

More recently, minimally invasive surgical procedures for treating vertebral compression fractures have been developed. These procedures generally involve the use of a cannula or other access tool inserted into the posterior of the effected vertebral body, usually through the pedicles. The most basic of these procedures is vertebroplasty, which literally means fixing the vertebral body, and may be done without first repositioning the bone.

Briefly, a cannula or special bone needle is passed slowly through the soft tissues of the back. Image guided x-ray, along with a small amount of x-ray dye, allows the position of the needle to be seen at all times. A small amount of polymethylmethacrylate (PMMA) or other orthopedic cement is pushed through the needle into the vertebral body. PMMA is a medical grade substance that has been used for many years in a variety of orthopedic procedures. Generally, the cement is mixed with an antibiotic to reduce the risk of infection, and a powder containing barium or tantalum, which allows it to be seen on the X-ray.

Vertebroplasty can be effective in the reduction or elimination of fracture pain, prevention of further collapse, and a return to mobility in patients. However, this procedure may not reposition the fractured bone and therefore may not address the problem of spinal deformity due to the fracture. It generally is not performed except in situations where the kyphosis between adjacent vertebral bodies in the effected area is less than 10 percent. Moreover, this procedure requires high-pressure cement injection using low-viscosity cement, and may lead to cement leaks in 30-80% of procedures, according to recent studies. In most cases, the cement leakage does no harm. In rare cases, however, polymethymethacrylate or other cement leaks into the spinal canal or the perivertebral venous system and causes pulmonary embolism, resulting in death of the patient.

More advanced treatments for vertebral compression fractures generally involve two phases: (1) reposition, or restoration of the original height of the vertebral body and consequent lordotic correction of the spinal curvature; and (2) augmentation, or addition of material to support or strengthen the fractured or collapsed bone.

One such treatment, balloon kyphoplasty (Kyphon, Inc.), is disclosed in U.S. Pat. Nos. 6,423,083, 6,248,110, and 6,235,043 to Riley et al., each of which is incorporated by reference herein in its entirety. A catheter having an expandable balloon tip is inserted through a cannula, sheath or other introducer into a central portion of a fractured vertebral body comprising relatively soft cancellous bone surrounded by fractured cortical bone. Kyphoplasty then achieves the reconstruction of the lordosis, or normal curvature, by inflating the balloon, which expands within the vertebral body restoring it to its original height. The balloon is removed, leaving a void within the vertebral body, and PMMA or other filler material is then injected through the cannula into the void as described above with respect to vertebroplasty. The cannula is removed and the cement cures to augment, fill or fix the bone.

Disadvantages of this procedure include the high cost, the repositioning of the endplates of the vertebral body may be lost after the removal of the balloon catheter, and the possible perforation of the vertebral endplates during the procedure. As with vertebroplasty, perhaps the most feared, albeit remote, complications concerning kyphoplasty are related to leakage of bone cement. For example, a neurologic deficit may occur through leakage of bone cement into the spinal canal. Such a cement leak may occur through the low resistance veins of the vertebral body or through a crack in the bone which was not appreciated previously. Other complications include additional adjacent level vertebral fractures, infection and cement embolization. Cement embolization occurs by a similar mechanism to a cement leak. The cement may be forced into the low resistance venous system and travel to the lungs or brain resulting in a pulmonary embolism or stroke.

Another approach for treating vertebral compression fractures is the Optimesh system (Spineology, Inc., Stillwater, Minn.), which provides minimally invasive delivery of a cement or allograft or autograft bone using an expandable mesh graft balloon, or containment device, within the involved vertebral body. The balloon graft remains inside the vertebral body after its inflation, which prevents an intraoperative loss of reposition, such as can occur during a kyphoplasty procedure when the balloon is withdrawn. One drawback of this system, however, is that the mesh implant is not well integrated in the vertebral body. This can lead to relative motion between the implant and vertebral body, and consequently to a postoperative loss of reposition. Additional details regarding this procedure may be found, for example, in published U.S. Patent Publication Number 20040073308, which is incorporated by reference herein in its entirety.

Still another procedure used in the treatment of vertebral compression fractures is an inflatable polymer augmentation mass known as a SKy Bone Expander. This device can be expanded up to a pre-designed size and (Cubic or Trapezoid) configuration in a controlled manner. Like the Kyphon balloon, once optimal vertebra height and void are achieved, the SKy Bone Expander is removed and PMMA cement or other filler is injected into the void. This procedure therefore entails many of the same drawbacks and deficiencies described above with respect to kyphoplasty.

In some cases of fractured or otherwise damaged bones, bone grafts are used to repair or otherwise treat the damaged area. In the United States alone, approximately half a million bone grafting procedures are performed annually, directed to a diverse array of medical interventions for complications such as fractures involving bone loss, injuries or other conditions necessitating immobilization by fusion (such as for the spine or joints), and other bone defects that may be present due to trauma, infection, or disease. Bone grafting involves the surgical transplantation of pieces of bone within the body, and generally is effectuated through the use of graft material acquired from a human source. This is primarily due to the limited applicability of xenografts, transplants from another species.

Orthopedic autografts or autogenous grafts involve source bone acquired from the same individual that will receive the transplantation. Thus, this type of transplant moves bony material from one location in a body to another location in the same body, and has the advantage of producing minimal immunological complications. It is not always possible or even desirable to use an autograft. The acquisition of bone material from the body of a patient typically requires a separate operation from the implantation procedure. Furthermore, the removal of material, oftentimes involving the use of healthy material from the pelvic area or ribs, has the tendency to result in additional patient discomfort during rehabilitation, particularly at the location of the material removal. Grafts formed from synthetic material have also been developed, but the difficulty in mimicking the properties of bone limits the efficacy of these implants.

As a result of the challenges posed by autografts and synthetic grafts, many orthopedic procedures alternatively involve the use of allografts, which are bone grafts from other human sources (normally cadavers). The bone grafts, for example, are placed in a host bone and serve as the substructure for supporting new bone tissue growth from the host bone. The grafts are sculpted to assume a shape that is appropriate for insertion at the fracture or defect area, and often require fixation to that area for example by screws, pins, cement, cages, membranes, etc. Due to the availability of allograft source material, and the widespread acceptance of this material in the medical community, the use of allograft tissues is likely to expand in the field of musculoskeletal surgery.

Notably, the various bones of the body such as the femur (thigh), tibia and fibula (leg), humerus (upper arm), radius and ulna (lower arm) have geometries that vary considerably. In addition, the lengths of these bones vary; for example, in an adult the lengths may vary from 47 centimeters (femur) to 26 centimeters (radius). Furthermore, the shape of the cross section of each type of bone varies considerably, as does the shape of any given bone over its length. While a femur has a generally rounded outer shape, a tibia has a generally triangular outer shape. Also, the wall thickness varies in different areas of the cross-section of each bone. Thus, the use of any given bone to produce an implant component may be a function of the bone's dimensions and geometry. Machining of bones, however, may permit the production of implant components with standardized or custom dimensions.

As a collagen-rich and mineralized tissue, bone is composed of about forty percent organic material (mainly collagen), with the remainder being inorganic material (mainly a near-hydroxyapatite composition resembling $3Ca_3(PO_4)_2 Ca(OH)_2$). Structurally, the collagen assumes a fibril formation, with hydroxyapatite crystals disposed along the length of the fibril, and the individual fibrils are disposed parallel to each other forming fibers. Depending on the type of bone, the fibrils are either interwoven, or arranged in lamellae that are disposed perpendicular to each other.

Bone tissues have a complex design, and there are substantial variations in the properties of bone tissues depending upon the type of bone (i.e., leg, arm, vertebra) as well as the overall structure. For example, when tested in the longitudinal direction, leg and arm bones have a modulus of elasticity of about 17 to 19 GPa, while vertebra tissue has a modulus of elasticity of less than 1 GPa. The tensile strength of leg and arm bones varies between about 120 MPa and about 150 MPa, while vertebra have a tensile strength of less than 4 MPa. Notably, the compressive strength of bone varies, with the femur and humerus each having a maximum compressive strength of about 167 MPa and 132 MPa respectively. Again, the vertebra have a far lower compressive strength usually of no more than about 10 MPa.

With respect to the overall structure of a given bone, the mechanical properties vary throughout the bone. For example, a long bone (leg bone) such as the femur has both compact bone and spongy bone. Cortical bone, the compact and dense bone that surrounds the marrow cavity, is generally solid and thus carries the majority of the load in major bones. Cancellous bone, the spongy inner bone, is generally porous and ductile, and when compared to cortical bone is only about one-third to one-quarter as dense, one-tenth to one-twentieth as stiff, but five times as ductile. While cancellous bone has a tensile strength of about 10-20 MPa and a density of about 0.7 g/cm$^3$, cortical bone has a tensile strength of about 100-200 MPa and a density of about 2 g/cm$^3$. Additionally, the strain to failure of cancellous bone is about 5-7%, while cortical bone can only withstand 1-3% strain before failure. It should also be noted that these mechanical characteristics may degrade as a result of numerous factors such as any chemical treatment applied to the bone material, and the manner of storage after removal but prior to implantation (i.e. drying of the bone).

Notably, implants of cancellous bone incorporate more readily with the surrounding host bone, due to the superior osteoconductive nature of cancellous bone as compared to cortical bone. Furthermore, cancellous bone from different regions of the body is known to have a range of porosities. For example, cancellous bone in the iliac crest has a different porosity than cancellous bone in a femoral head. Thus, the design of an implant using cancellous bone may be tailored to specifically incorporate material of a desired porosity.

There remains a need in the art to provide safe and effective devices and methods for augmentation of fractured or otherwise damaged vertebrae and other bones, preferably devices that may be implanted utilizing minimally invasive methods of implantation.

SUMMARY OF THE INVENTION

A flexible chain according to one embodiment comprises a series or other plurality of preferably solid, substantially non-flexible body portions (also referred to as bodies or beads) and a series of flexible link portions (also referred to as links or struts). The preferably solid, substantially non-flexible body portions preferably are capable of withstanding loads that are applied in any direction, and the flexible link portions of the implant preferably are disposed between the substantially non-flexible body portions and preferably are flexible in any direction, although they may be flexible in only selected or desired directions. The bodies may be substantially solid, semi-solid or hollow and preferable of sufficient strength to support the loads typical for the body location in which they are implanted. The link portions may be solid, semi-solid, or hollow and preferably of sufficient flexibility to allow the adjacent bodies to touch one another upon bending of the elongate member or chain. The material of both portions, the flexible link and non-flexible body portions, preferably is the same and form one single, flexible monolithic chain (FMC).

In one aspect of the invention, an apparatus for augmentation of body tissue, for example bone, comprises a flexible elongated member, or chain, having a longitudinal length substantially larger than its height or its width. The flexible elongated member comprises a plurality of substantially non-flexible bodies and a plurality of substantially flexible links interconnecting the bodies. The bodies and links are connected end-to-end to form the elongated member, wherein the elongated member is formed of a biocompatible material.

The bodies may be different sizes and shapes than the links or they may be the same shape, same size, or both. In addition, each body and link may be a different size and shape than other bodies or links. In one embodiment, the beads can be shaped so that they can fit together to minimize interstial spaces. For example, the beads may be shaped as cubes or other polyhedrals that can be stacked together in such a way that there is little space between beads, or a predetermined percentage range of interstial space.

The elongated member may be formed as an integral monolithic chain, which may be formed of bone, such as, for example, allograft bone. The flexible links may be formed of bone that has been demineralized to a greater extent than the bodies. Optionally, a coating may be applied to at least a portion of the elongated member, e.g. a coating comprising a therapeutic agent, a bone cement, an antibiotic, a bone growth stimulating substance, bone morphogenic protein (BMP) or any combination thereof. Therapeutic agents, or drug agents (e.g., antibodies), or biologics (e.g., one or more BMPs) can be coated, or attached via peptides, adsorbed, sorbed or in some other way perfused onto or into the elongated member; either the bodies, the links or both. In some embodiments, the coating may comprise a bone cement that may be activated upon insertion into the bone. In other embodiments, at least a portion of the bodies comprise an outer surface configured to promote bone in-growth.

In another aspect, a flexible chain implant may be impacted or inserted into a cavity, void or hollow space, e.g., through a small narrow opening. Such cavities may be, for example, voids in long bones, intervertebral disc spaces or vertebral bodies. Such voids may have occurred due to infections, disease, trauma fractures, degenerative disc disease process, tumors or osteotomies. In other embodiments, a void may be created by using a tool to compact or remove cancellous or cortical bone or other tissue prior to implantation. The chain may thereafter be implanted to fill the created void. Depending on the insertion or impaction force and depending on the amount or the length of chain devices inserted, the device will fill and/or support the tissue structure, preferably bone structure to a restored size and/or height. In an alternative embodiment, no void or cavity may be present, and even if a void or cavity is present the chain implant or elongated member may be inserted and/or implanted in a manner to compact the material and bone cells within the bone and to further fill the bone in a manner that it can better support a load and preferably fill the bone in a manner to restore its original and/or treated size and height.

In another aspect, one or more flexible monolithic chains may be implanted into diseased, damaged or otherwise abnormal bones to treat, for example, long bone infections, comminuted complex fractures, tumor resections and osteotomies. An FMC device may also be used to treat disease or abnormal pathology conditions in spinal applications, including, for example, degenerative disc disease, collapsed intervertebral discs, vertebral body tumor or fractures, and vertebral body resections. The elongated member or chain device can be used as a preventive measure to augment a bone, spinal disc or an implant, e.g., and intervertebral body implant to promote fusion. The elongated member may be used within a vertebra or between two vertebra. The elongated member or chain also may be used for example in an intervertebral body fusion procedure, for example, as an implant inserted into the disc space between two vertebra, as an implant inserted into and retained by the disc annulus, or in combination with an additional implant inserted in the disc space between two vertebra.

In another embodiment, a kit comprises various combinations of assemblies and components according to the present invention. A kit may include, for example, a package or container comprising an elongated member, for example an FMC device, and a cannula or other introducer or device for implanting the elongated member. In other embodiments, a kit may comprise instruments to create a cavity (e.g., balloon catheter), an FMC device and a cement or other filler material and/or a syringe or other apparatus for injecting a FMC device and/or such filler material into a vertebral body.

BRIEF DESCRIPTION OF THE DRAWINGS

The present invention can be better understood by reference to the following drawings, wherein like references numerals represent like elements. The drawings are merely exemplary to illustrate certain features that may be used singularly or in combination with other features and the present invention should not be limited to the embodiments shown.

FIG. 11A is a side view of a screw device for driving a chain implant through an introducer.

FIG. 11B is an end view of a screw device for driving a chain implant through an introducer.

FIG. 12 is a side view of a plunger device for driving a chain implant through an introducer.

FIG. 13 is a side view of a sprocket device for driving a chain implant through an introducer.

DETAILED DESCRIPTION

Figure 1:
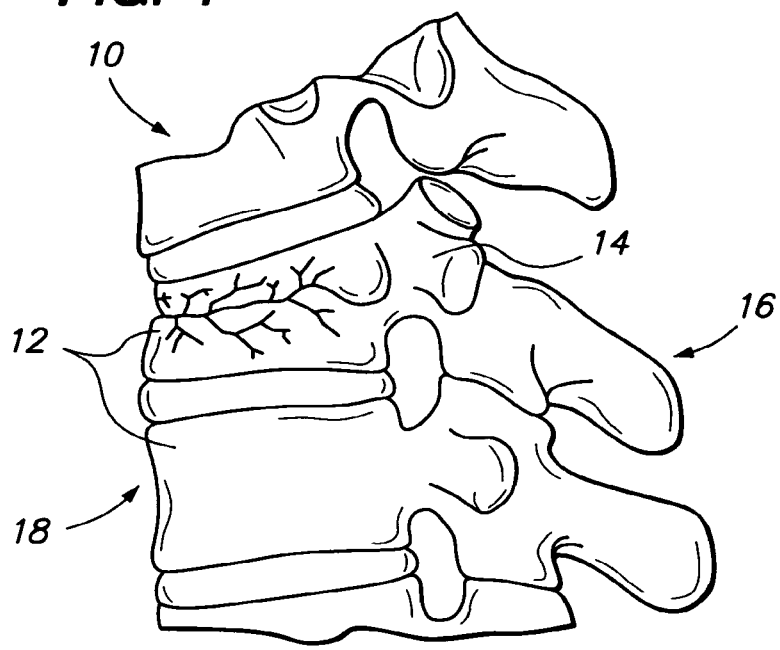
FIG. 1 is a side view of a portion of a spine with a vertebral compression fracture.

Referring to FIG. 2, a chain 200 (sometimes referred to as an elongated member) comprises one or more bodies 210 (sometimes referred to as beads). Chain 200 is preferably a monolithic chain, e.g., formed from a single, common material or type of material forming an integral structure. Bodies 210 are preferably substantially non-flexible, and may be solid, semi-solid, porous, non-porous, hollow, or any combination thereof. Chain 200 may also comprise one or more linking portions 220, also sometimes referred to as struts or links 220. Struts 220 may be disposed between each pair of adjacent bodies 210. Struts 220 are preferably substantially flexible or semiflexible, e.g. to allow for bending of the chain 200 between bodies 210.

Bodies 210 of chain 200 are preferably formed of bone, e.g., cortical bone, cancellous bone or both, but preferably cortical bone. In other embodiments, chain 200 may be comprised of any biocompatible material having desired characteristics, for example a biocompatible polymer, metal, ceramic, composite or any combination thereof. Bodies 210 may be absorbable or resorbable by the body. For some applications, the bodies 210 preferably have osteoinductive properties or are made at least partly from osteoinductive materials. The outer circumferential shape of the body may be the same as adjacent links. Alternatively or in addition, the outer circumferential shape of the body may be the same size as adjacent links. Bodies 210 may be of uniform or non-uniform size, shape and/or materials, and may be linked in series, for example by one or more flexible or semi-flexible linking portions 220, which can form struts of any desired length between bodies 210. Linking portions are preferably, although not necessarily, formed of the same material as bodies 210.

A chain 200 may have any desired number of linked bodies 210, and may have a first end 202 and a second end 204. In other embodiments, chain 200 may be formed in a loop, ring, or other configuration having no ends, or may be configured to have multiple extensions and/or multiple ends, for example like branches of a tree.

The one or more linking portions 220 may be comprised of any biocompatible material having desired characteristics of flexibility, strength, and the like. In preferred embodiments, linking portions 220 may be formed, at least in part, of substantially the same material as bodies 210. In some embodiments, chain 200, including bodies 210 and/or linking portions 220, may be resorbable. The bodies 210 may be of uniform or non-uniform size, and may be spaced by linking portions 220 at uniform or non-uniform increments.

Figure 2A:
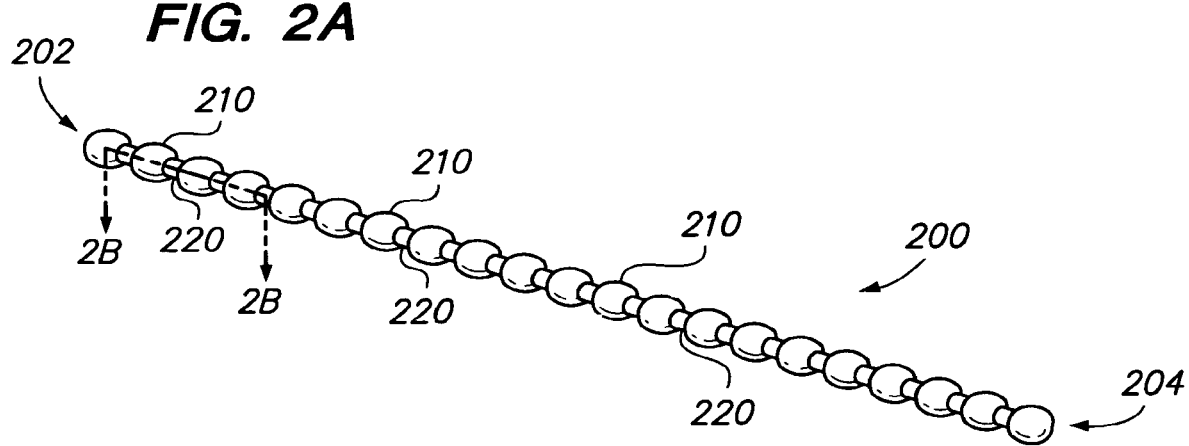
FIG. 2A is a side view of a flexible monolithic chain according to an embodiment of the present invention.
Figure 2B:
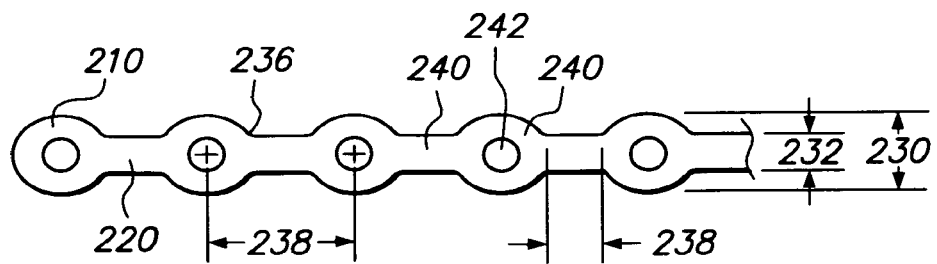
FIG. 2B is a close-up cross-sectional side view of the flexible monolithic chain of FIG. 2A taken through line B-B.

FIG. 2B is a close up cross-sectional view of chain 200, taken at line B-B in FIG. 2A. In this example, chain 200 is a monolithic chain, with bodies 210 and flexible portions 220 formed from a uniform material, e.g., bone. Although bodies 210 are shown as substantially spherical, and linking portions 220 are shown as substantially cylindrical, numerous other shapes are contemplated. In fact, chains 200, including body 210 and/or linking portion 220, may be of any desired shape, such as for example, cylindrical, elliptical, spherical, rectangular, etc. Body 210 and/or linking portion 220 may also be of any particular cross sectional shape such as round hexagonal, square, etc. Bodies 210 and linking portions 220 may have the same or different shapes. In certain embodiments the configurations of bodies 210 may vary within a chain 200, for example as described herein with respect to FIGS. 5 and 10. Alternatively or in addition thereto, the configuration of links 220 may vary within a chain. In one embodiment, the bodies can be shaped so that they fit together to minimize interstitial spacing or provide a predetermined range of interstitial spacing.

All dimensional aspects of the chain 200 can be made to fit any particular anatomy or delivery device. For example, for applications of vertebral body augmentation, the diameter 230 of bodies 210, e.g., as shown in FIG. 2B, may be between about 1 mm and about 15 mm, preferably between about 2 mm and about 8 mm, or more preferably between about 4 mm and about 6 mm. Preferably, the non-flexible bodies 210 are larger in shape and size than the flexible struts 220. For example, height 232 of struts 220 may be between about 0.5 mm and about 8 mm, preferably between about 0.8 mm and about 4 mm, and may depend in part upon the size of bodies 210. Struts 220 may have any desired length 238, e.g., between about 0.5 mm and about 5.0 mm, preferably between about 1.5 mm and 3.5 mm, or greater than 5 mm. Similarly, distance 234 between bodies 210 may be any desired distance, e.g., depending upon the size of bodies 210 and/or length 238 struts 220. In some embodiments, for example, distance 234 may be between about 4 mm and about 15 mm, or between about 6 mm and about 10 mm. The junctions between bodies 210 and struts 220 may have a radius 236 of any desired dimension, e.g., less than 1.0 mm, between about 1.0 mm and about 2.0 mm, or greater than about 2.0 mm.

In some embodiments, each of the bodies 210 and struts 220 of a chain may be of the same configuration and/or dimensions as other bodies 210 and struts within the chain 200. In other embodiments, bodies 210 and/or struts 220 within a chain may have different configurations or dimensions. In still other embodiments, the non-flexible bodies 210 and flexible portions 220 may be of the same shape and size to form a relatively uniform structure, for example as shown in FIG. 4.

A chain 200 may be made as long as practical for a particular application. For example, an exemplary chain 200 for implantation into a bone may be about 100 mm in length. In other embodiments, chain 200 may be of other lengths, for example less than about 1 mm, between about 1 mm and about 100 mm, or greater than 100 mm. In some embodiments, two or more chains 200 and/or other implants may be used in combination with each other. Chain 200 may be connected end to end to form larger chains.

While the present invention is preferably directed to the creation of implants from allograft material, the present invention may also be applied to implants that utilize other materials, including but not limited to the following: xenograft, autograft, metals, alloys, ceramics, polymers, composites, and encapsulated fluids or gels. Furthermore, the implants described herein may be formed of materials with varying levels of porosity, such as by combined bone sections from different bones or different types of tissues and/or materials having varying levels of porosity.

Also, the implants described herein may be formed of bone materials with varying mineral content. For example, cancellous or cortical bone may be provided in natural, partially demineralized, or demineralized states. Demineralization is typically achieved with a variety of chemical processing techniques, including the use of an acid such as hydrochloric acid, chelating agents, electrolysis or other treatments. The demineralization treatment removes the minerals contained in the natural bone, leaving collagen fibers with bone growth factors including bone morphogenic protein (BMP). Variation in the mechanical properties of bone sections is obtainable through various amounts of demineralization. Advantageously, use of a demineralizing agent on bone, e.g., cortical or cancellous bone, transforms the properties of the bone from a stiff structure to a relatively pliable structure. Optionally, the flexibility or pliability of demineralized bone may be enhanced when the bone is hydrated. Any desired portions of bone components, e.g., link portions 220 or any other desired portion, may be demineralized or partially demineralized in order to achieve a desired amount of malleability, elasticity, pliability or flexibility, generally referred to herein as "flexibility". The amount of flexibility can be varied by varying in part the amount of demineralization.

In some embodiments, flexibility of demineralized or partially demineralized regions may be further enhanced by varying the moisture content of the implant or portions thereof. Bone components initially may be provided with moisture content as follows: (a) bone in the natural state fresh out of the donor without freezing, (b) bone in the frozen state, typically at −40° C., with moisture content intact, (c) bone with moisture removed such as freeze-dried bone, and (d) bone in the hydrated state, such as when submersed in water. Using the expansion and contraction properties that can be obtained during heating and cooling of the bone material, and the concomitant resorption of moisture along with swelling for some bone material, permits alternate approaches to achieving a desired flexibility of an implant within a bone or other region.

The implants may be formed entirely from cortical bone, entirely from cancellous bone, or from a combination of cortical and cancellous bone. While the implants may be created entirely from all bone material, it is also anticipated that one or more components or materials may be formed of non-bone material, including synthetics or other materials. Thus, while the implants disclosed herein are typically described as being formed primarily from bone, the implants alternatively may be formed in whole or in part from other materials such as stainless steel, titanium or other metal, an alloy, hydroxyapatite, resorbable material, polymer, or ceramic, and may additionally incorporate bone chips, bone particulate, bone fibers, bone growth materials, and bone cement. Also, while solid structures are described herein, the structure optionally may include perforations or through bores extending from one outer surface to another outer surface, or recesses formed in outer surfaces that do not extend through inner surfaces (surface porosity), or recesses formed internally. Surface texture such as depressions and/or dimples may be formed on the outer surface. The depressions and/or dimples may be circular, diamond, rectangular, irregular or have other shapes.

The flexible monolithic chain devices described herein may be used to treat disease and pathological conditions in general orthopedic applications such as long bone infections, comminuted complex fractures, tumor resections and osteotomies. Additionally the device can be used to treat disease and pathological conditions in spinal applications, such as, for example, degenerative disc disease, collapsed intervertebral discs, vertebral body tumor or fractures, vertebral body resections or generally unstable vertebral bodies. In other embodiments, a flexible monolithic chain device may be used in maxillofacial applications or in non-fusion nucleus replacement procedures.

FIG. 3 shows an example of a method 300 for fabricating a monolithic chain device 200 out of bone material 310. In this example, allograft femoral bone 310 is used as a base material, preferably, cortical allograft bone. Other bones may be used for forming implants, for example, radius, humerus, tibia, femur, fibula, ulna, ribs, pelvic, vertebrae or other bones.

Figure 3A:
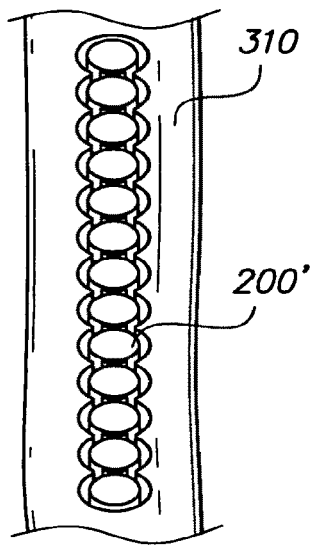
FIGS. 3A-D is an illustration depicting a method of fabricating a flexible monolithic chain.
Figure 3B:
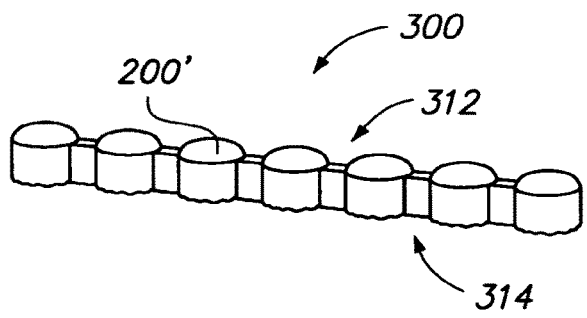
Figure 3C:
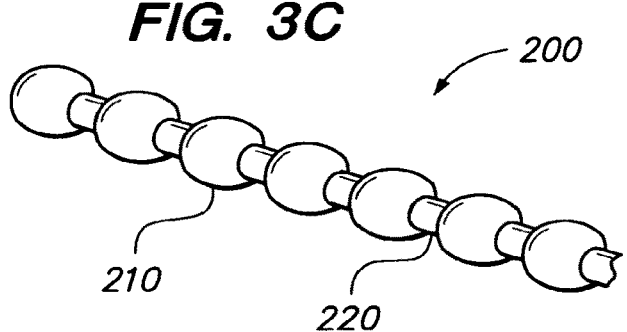
Figure 3D:
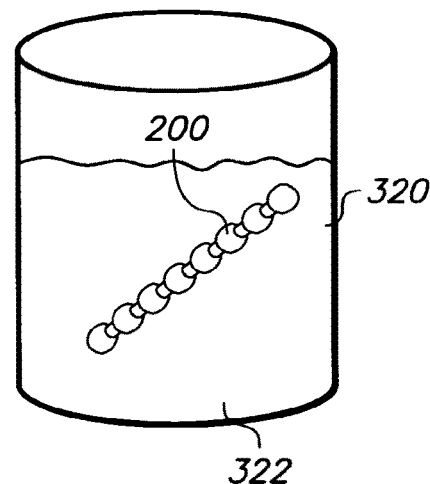

As shown in FIG. 3A, an initial step comprises machining a rough monolithic chain 200', having a desired general shape, out of the raw material 310, preferably bone. For example, conventional milling and/or other fabrication techniques may be used. Device 200, may have any desired shape, for example including generally elliptical or spherical bodies 210 separated by cylindrical linking portions 220 as shown. Alternatively, chain 200 may be formed of a substantially uniform shape as shown, for example, in FIG. 4.

After machining the general desired shape in step A of FIG. 3, the rough monolithic device 200' may then be removed from the raw material 310, as shown for example in step B. In this example, an upper side 312 of the rough device 200' has been fabricated to have a desired general shape as described above. An opposite side 314, however, may include excess material that was not removed in step A.

In step C of the exemplary method of FIG. 3, opposite side 314 is machined to remove excess material, for example using conventional milling methods. Side 312 may also be further machined or shaped as desired, in order to form a monolithic chain device 200 having the desired shapes and configurations of bodies 210 and linking portions 220.

In step D, the shaped chain 200, if formed of bone, may be demineralized, e.g., in container 320 containing a demineralizing solution 322 (e.g., hydrochloric acid) or using another method. Demineralization may be allowed to occur for a specified amount of time, for example to allow the smaller, lower volume portions 220 of the device 200 to become more flexible or elastic, while the larger bodies 210 of the device remain structurally intact and substantially rigid. The amount of time and/or the concentration or composition of the demineralizing solution may be varied to provide the desired amount of flexibility or elasticity.

In some embodiments, this secondary process of demineralization can be applied to specific portions of the device 200, e.g., by masking or shielding the portions that do not or should not be treated. For example, by masking the non flexible portions 210, the flexible portions 220 can be partially or entirely demineralized, and the non-flexible portions 210 may retain their original mineralized state prior to the masking. Alternatively, an allograft device may be submerged entirely into demineralization acid without masking any portions of the device. Due to the relatively smaller shape and size of the flexible portions 220, including the surface area exposed to the demineralized agent, and depending for example upon the amount of exposure to the demineralization acid, the flexible portions 220 may demineralize entirely, or at least substantially more than the larger portions 210, which may undergo only surface demineralization. Therefore, the smaller portions 220 may become flexible and elastic while the larger portions 210 may remain relatively stiff and substantially non-flexible. For example, FIG. 2B shows regions 240 that are substantially demineralized and regions 242 that have substantially their natural or original composition and mineralization content.

The following Table 1 provides examples of demineralization times of four monolithic chains having different strut configurations. Each of the chains were formed of cortical allograft bone and had body portions 210 that were approximately 5 mm in diameter. Configurations and dimensions of the struts 220 differed between the samples. In all four samples, the struts were fully demineralized between about 3½ and 4 hours, while the beads were demineralized to an extent, but were not fully demineralized across their entire thickness. Strut dimensions correspond to distance 238 in FIG. 2B, while strut radius corresponds to radius 236 in FIG. 2B. Full flexibility is considered to be the condition when the chain can be bent until two adjacent beads contact each other without the chain cracking or breaking. While the foregoing is one manner to measure sufficient flexibility, other measures of flexibility are also contemplated and the invention should not be limited by such measure of flexibility. For example, less than full flexibility may be sufficient and desirable for insertion into vertebrae to augment and support the vertebral end plates.

TABLE 1

Examples of demineralization times for 5 mm diameter chains having different strut configurations.

| Sample | Strut Dimensions (w × h × l, in mm) | Strut Radius* (mm) | Chain Length (mm) | Demineralization Time** (min.) |
|---|---|---|---|---|
| 1 | 1.5 × 1.5 × 3.2 | — | 76 | 210 |
| 2 | 1.5 × 1.5 × 3.2 | 1.57 | 101 | 255 |
| 3 | 1.0 × 1.4 × 3.0 | 1.57 | 93.35 | 180 |
| 4 | 1.5 × 1.5 × 3.0 | 1.57 | 101 | 180 |

*Radius between body 210 and strut 220 on top and bottom only
**Time in hydrochloric acid 1N solution to achieve full flexibility Table 2 below provides an example of approximate incremental changes in flexibility of strut portions 220 of a sample, e.g., Sample 1 of Table 1, as a function of duration of exposure to the hydrochloric acid bath.

TABLE 2

Incremental changes in flexibility of struts with exposure to acid bath.

| Exposure Time (min) | Flexibility (% of maximum) |
|---|---|
| 0-5 | 0 |
| 5-10 | 0 |
| 10-15 | 10 |
| 15-20 | 15 |
| 20-30 | 25 |
| 30-45 | 35 |
| 45-90 | 50 |
| 90-140 | 70 |
| 140-200 | 85 |
| 200-240 | 100 |

Of course, other samples will attain different flexibility in different exposure times depending upon a host of factors, including concentration of acid bath, chain dimensions, temperature, original bone sample mineralization and condition, etc.

Various other configurations and methods for manufacturing monolithic or other chain implants may be used. The choice of methods may depend, at least in part, on the material or materials to be used in the particular chain device 200. If the device is made of a biocompatible polymeric material, the device can be manufactured by using conventional manufacturing methods such as but not limited to milling and turning. Alternatively, if the chain device 200 is made out of a biocompatible polymeric material, the entire device can also be injection molded.

If the chain 200 is made of a metallic material, it can be manufactured by using conventional manufacturing methods such as but not limited to milling and turning. However, the flexible components may undergo secondary processes such as annealing. The secondary process can be limited to the flexible portions of the device only, for example by masking or shielding the non-flexible portions.

In some embodiments, a chain implant 200 can be formed of any type of biocompatible material that will allow for sufficient flexibility in areas of reduced material sections (e.g., relatively narrow and flexible portions 220), while having larger sections (e.g., bodies 210) that are substantially rigid and allow for load bearing characteristics. The reduced material portions 220 may be flexible, pliable, or have elastic properties in all directions preferably without fracturing or breaking. Alternatively, the reduced material portions 210 may allow for fracture during device 200 insertion, or at another stage in a method, to allow for proper void filling. Materials may be metallic and include but are not limited to titanium and steels. Polymeric and alternatively allograft tissue materials can be used. Instead of or in addition to bone device 200 may comprise one or more other materials, e.g., a metal (titanium, a steel, or other metal), an alloy, or a polymer. In some embodiments, the material of the device 200 may have osteoconductive, osteoinductive, and/or osteogenic properties. In other embodiments, the implant device 200 may be made out of non-monolithic materials.

Figure 4A:
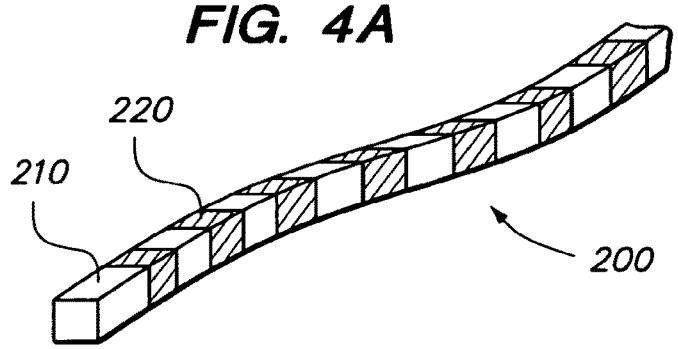
FIGS. 4A-C are perspective views of other embodiments of a flexible monolithic chain having flexible portions and non-flexible portions with substantially uniform dimensions.
Figure 4B:
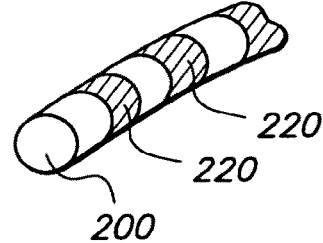
Figure 4C:
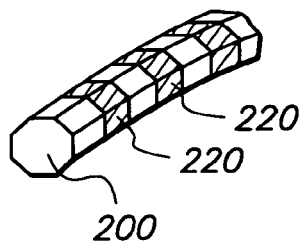

Referring to FIGS. 4A-C, a chain 200 may have any desired geometric configuration. For example, rigid portions 210 and flexible portions 220 may have the same or different shapes, such as cubes, cylinders, any polyhedral shapes, balls, banana or kidney shaped, or any combination thereof. Portions 210 and/or 220 may have any desired cross-sectional shape, such as for example rectangular, circular, elliptical, pentagonal, hexagonal, etc. The flexible 220 and non-flexible 210 portions may be of the same shape to form relatively uniform shaped structures as shown in FIGS. 4A-C.

Figure 5:
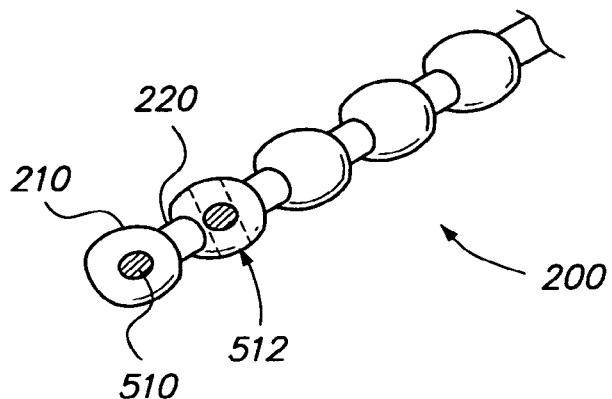
FIG. 5 is a perspective, cross-sectional view of another embodiment of a flexible monolithic chain.

As shown in FIG. 5, one or more bodies 210 may have cavities 510 or central holes 512. Such holes 512 or cavities 510 may be empty or may be filled, for example with a cement, bone filler, adhesive, graft material, therapeutic agent, or any other desired materials. The filling material may incorporate radiopaque agents so that the chain, or bodies can be visualized during and after a procedure. In other embodiments, an implant device 200 may be coated with different substances that will support and promote bone healing, reduce infections and/or deliver therapeutic agents to the treated site. For example, the device 200 or portions thereof may be coated with antibiotics, BMP, bone growth enhancing agents, porous or non-porous bone ingrowth agents, therapeutic agents, etc. The implant may be coated with a material that may incorporate a radiopaque agent so that the implant may be visualized during or after implantation. In addition, therapeutic agents, drug agents, BMPs, tissue growth enhancing agents, osteoinductive agents may be absorbed, sorbed or other wise perfused onto or into some portion of the chain implant. Additionally, the solid, non-flexible portions 210 may have cavities, axial or side holes or a combination thereof that can be filled with different substances or agents.

Figure 6A:
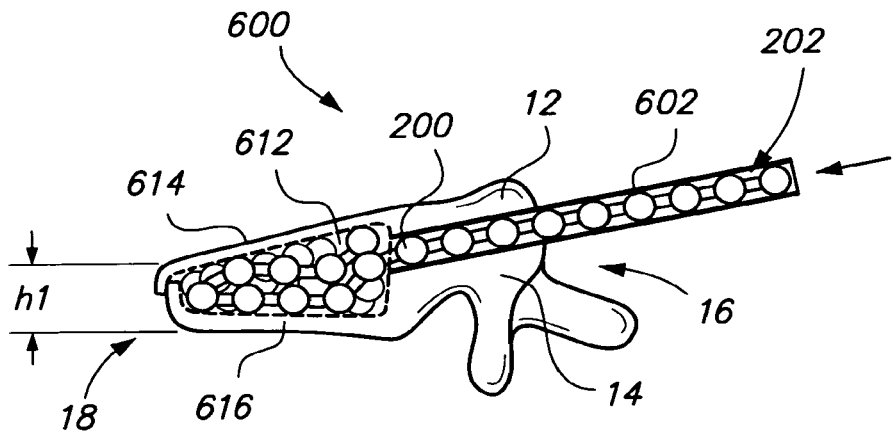
FIGS. 6A and B are side cross-sectional views of a flexible monolithic chain being implanted within a fractured vertebral body.
Figure 6B:
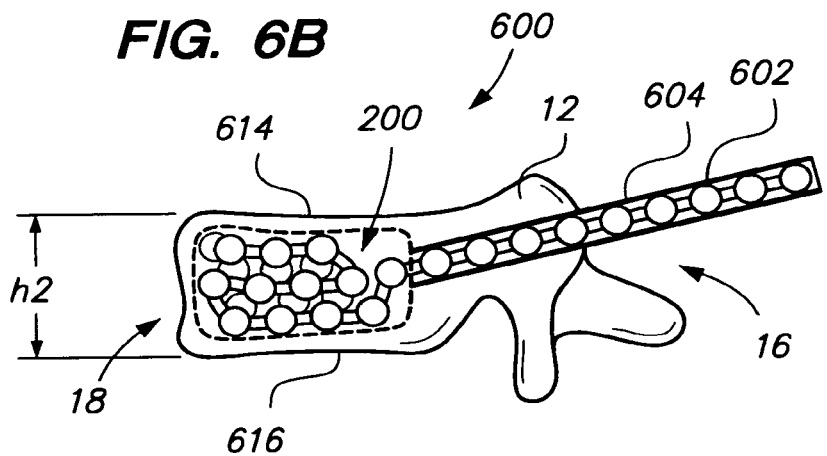

As shown in FIGS. 6A and 6B, a minimally invasive method 600 of augmenting a damaged vertebral body 12, e.g., following a vertebral compression fracture, may comprise implanting one or more chains 200 into an inner portion 612 of a vertebral body 12 between endplates 614 and 616. Of course, one or more chains 200 may be implanted as a preventive measure to augment a vertebra before compression or a compression fracture. A hole may be formed in the outer coritcal shell of vertebral body 12 by a trocar, drill or other instrument. Chain 200 may then be implanted, for example, through a cannula 602 or other introducer inserted into vertebral body 12. Suitable procedures and materials for inserting a cannula through which chain 200 may be introduced are known in the art, and may be similar to those described above for kyphoplasty and other procedures. For example, cannula 602 may be introduced through the posterior portion 16 of vertebral body 12, e.g., through pedicle 14 (e.g., transpedicular approach). A chain 200 may be inserted and may compact the cancellous and osteoporotic bone inside the vertebral body.

Prior to insertion of the cannula, a passageway may be formed into the interior of the vertebral body, for example using a drill or other instrument. The chain 200 may then be inserted through the passageway, and may compact or compress the bone material inside the vertebral body. Alternatively, after the passageway is formed in the vertebral body, instruments such as, for example, curettes or balloon catheter may be used to compress and compact the bone inside the vertebral body to create a cavity. The instruments may then be removed. Alternatively, the balloon portion of the catheter may remain within the vertebral body or may form a container for the implant. The cavity in the vertebral body also may be formed by removing bone material as opposed to compacting the bone. For example, a reamer or other apparatus could be used to remove bone material from the inside of the vertebral body.

Whether a cavity is first formed in the bone structure or the chain(s) are inserted without first creating a cavity, as more linked bodies 210 of chain 200 are inserted into vertebral body 12, they may fill central portion 612 and provide structural support to stabilize a vertebral body. In a vertebra that has collapsed, as the chain implant 200 fills central portion 612 the implant, and particularly the linked bodies 210, can push against the interior or inner sides of endplates 614 and 616, thereby tending to restore vertebral body 12 from a collapsed height h1 to its original or desired treated height h2 and provide structural support to stabilize vertebral body 12. Instead of using the insertion of the chain implant to restore the height of the vertebra, an instrument can be inserted through the passageway to restore the height of the vertebra and plates. For example, a balloon catheter can be inserted to restore vertebra end plates, or an elongated instrument that contacts the inside of the end plates and pushes on them may be utilized. Additionally, the flexibility of one or more portions 220 between bodies 210 may allow bending of chain within space 612, e.g., in a uniform pattern or in a non-uniform or tortuous configuration, to aid in ensuring a thorough integration of the implant 200 within the bone 12. The configuration of bodies 210 attached by flexible portions also may permit bending to substantially fill the cavity and/or vertebral bone so no large pockets or voids are created or remain which may result in weak spots or a weakened bone structure. The flexible links may also allow the chain to collapse and possibly become entangled so that it becomes larger than its insertion hole so that it cannon be easily ejected.

In other embodiments, chain 200 may be inserted into a bone such as a vertebral body 12, e.g., through the lumen 604 of a cannula 602 or other sheath, and such sheath may be removed after implantation within the bone 12. In such embodiments, chain 200, or a portion thereof, may remain in vertebral body 12, for example, to continue augmenting the vertebra and maintain proper lordosis. In other embodiments, PMMA or another bone cement or filler (for example bone chips) may be inserted sequentially or simultaneously into vertebral body 12, e.g., through shaft and/or a cannula 602, along with bodies 210 to further enhance fixation or repair of the damaged region. Alternatively, only a plug of bone cement may be inserted into the hole that was initially formed to insert chains 200 (e.g., plug 812 of FIG. 8A). The plug may cover the insertion hole to prevent the implant (chains) from being removed or ejected. In other embodiments, some or all of bodies 210 of chain 200 may be removed after repositioning the bone, and PMMA or another bone cement or filler may be injected into a void created by chain 200. Alternatively a bone growth promoting filler may be inserted into vertebral body 12 and a plug of bone cement utilized to hold the linked bodies and filler material in the vertebrae.

In some embodiments, flexible chain 200 may be coated with an adhesive, such that chain 200 may be inserted into vertebral body 12 in a flexible state and may become tangled and/or convoluted during or after insertion. After insertion, bodies 210 may become attached together by the adhesive so that the flexible chain becomes a mass that may be locked into the vertebral body, or otherwise secured such that chain 200 may not be easily removed through the insertion opening.

In other embodiments, linked bodies 210 may be coated with an adhesive and chain may be inserted, with or without becoming tangled or convoluted, into a vertebral body. During or after insertion of some or all linking bodies 210 of a chain 200, a portion of chain 200 may be exposed to an energy source (e.g., an ultraviolet light, ultrasonic radiation, radio waves, heat, electric filed, magnetic field), for example to activate the adhesive, such that the exposed portion of chain 200 becomes joined to form a mass, or becomes rigid, or both, thereby further augmenting the vertebral body 12 and/or preventing removal or ejection of chain 200 through the insertion opening.

Figure 7:
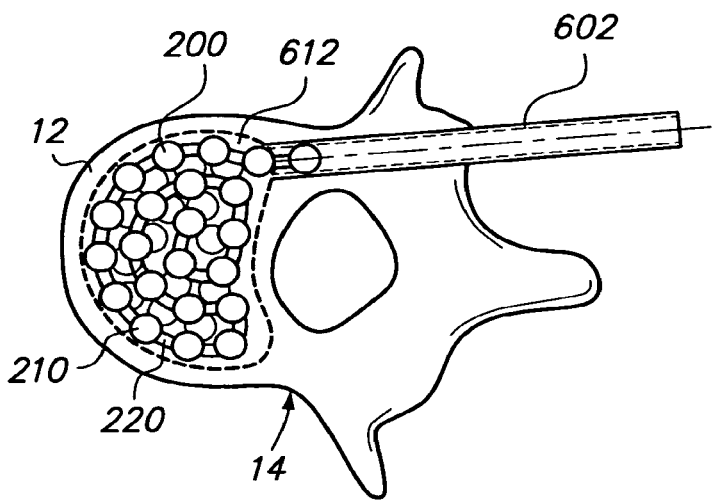
FIG. 7 is a cross-sectional top view of a flexible monolithic chain implanted within a vertebral body.

FIG. 7 is a top cross-sectional view illustration of a vertebral body 12 having one or more chains 200 implanted within portion 612 of vertebral body 12. The one or more chains 200 may comprise a plurality of bodies 210, which may be joined in series by one or more linking portions as described above. One or more cannulae 602, each for example having a lumen 604 of sufficient size for passing linked bodies 210, can be used to implant chain 200 into vertebral body. The one or more cannulae 602 may be inserted into vertebral body 12, preferably through pedicles 14. In some embodiments, the one or more cannulae 602 may be left within vertebral body 12, and remain extending from pedicles 14, for example held in place by sutures (not shown).

Figure 8A:
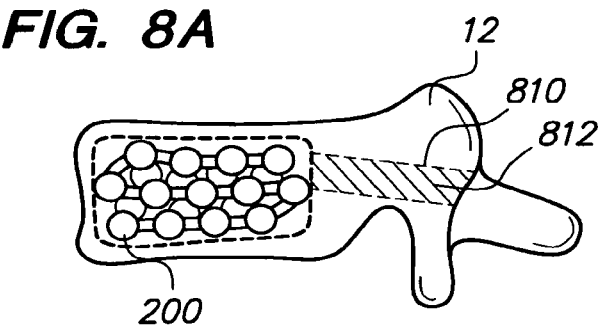
FIG. 8A is a cross-sectional side view of a vertebra having a flexible monolithic chain implanted within a vertebral body.
Figure 8B:
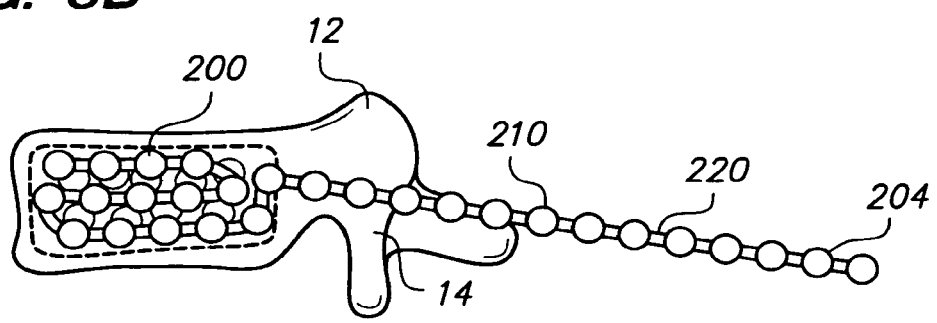
FIG. 8B is a cross-sectional side view of a vertebra having an implanted flexible monolithic chain as in FIG. 8A, showing an end of the chain extending from the vertebra.
Figure 8C:
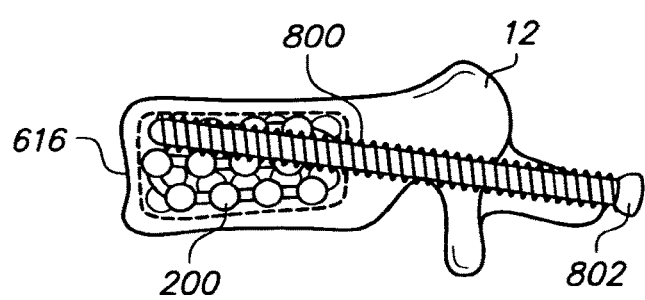
FIG. 8C is a cross-sectional side view of a vertebra having an implanted flexible monolithic chain as in FIG. 8A, and further including a pedicle screw implant.

In some embodiments, chains 200 may be implanted completely within vertebral body 12 as shown in FIG. 8A, and the cannulae or other introducer may be removed. The chains may remain entirely within the interior of the bone. A passageway 810 through which chains 200 were inserted may be filled with a plug 812, e.g., a bone cement plug. Alternatively, as shown in FIG. 8B, an end 204 of chain 200 may be left extending through the insertion hole of the bone, for example through the pedicle 14 of vertebra 12. In other embodiments, as shown in FIG. 8C, other implants or apparatus, such as for example a bone screw 800, may be inserted into vertebral body 12 in conjunction with chain implant 200 to further augment vertebral body 12. The extended end 204 or additional implant 800 may be used, for example, as an anchoring element for imparting an eternal force on vertebra to reposition the vertebra 12. Screw 800 may be inserted into the opening used to insert the chains, and may further serve as a plug to prevent removal or ejection of the chains. Screw 800 may be hollow or solid, and may be comprised of stainless steel, a metal alloy, a ceramic, polymer, composite or any other desired material. In some embodiments, screw 800 may be hollow, e.g., including a lumen such as lumen 604 of cannula 602, and used as an introducer to create a passage for passing chain 200 into vertebral body 12. A bone cement or other material may be injected into vertebral body 12 to further secure implants 200 and/or 800 and augment vertebral body 12. The bone cement or other material may be inserted through the cannulation of the screw.

Figure 9A:
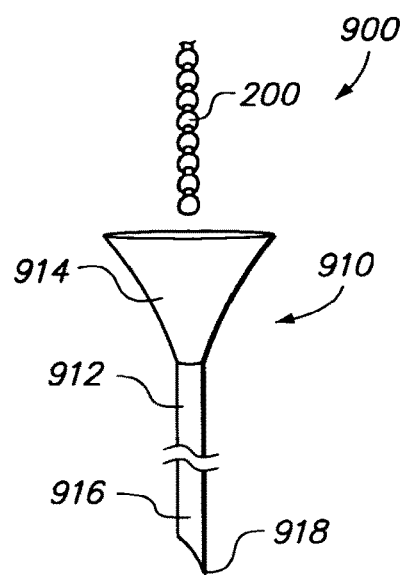
FIGS. 9A-D are top views depicting a minimally invasive method for implanting a flexible monolithic chain within a vertebral body.

FIGS. 9A-D show another example of a flexible monolithic chain device being implanted into vertebral body. In FIG. 9A, after a chain device 200 is unpacked, e.g., from a sterile package or container, it may be placed into an introducer or delivery device 910 that aids in insertion and/or impaction of the chain 200 to a desired cavity, void, space or interior of a bone. In this example, delivery device 910 has an elongated cannula-like shaft 912 having a lumen through which chain 200 may pass. Device may have a funnel 914 or other structure to facilitate loading of the chain 200 and/or for holding a portion of the chain 200 prior to implantation. An insertion end 916 of the insertion device 910 may have a tip 918, which may be blunt, pointed, tapered or otherwise configured as desired to facilitate insertion of end 916 into a bone or other structure.

Figure 9B:
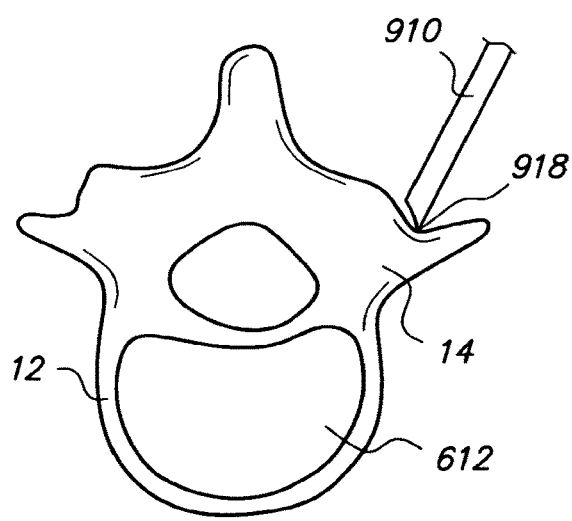

FIG. 9B shows end 916 of insertion device 910 being inserted through pedicle 14 of vertebra 12, such that tip 918 enters interior portion 612 of the vertebral body. An access hole may be formed in the outer cortical shell of the vertebral body by a trocar, drill or other instrument to provide a passage through which introducer 910 device may be inserted. After insertion of end 916 of delivery device 910 into the desired region, e.g., into a vertebral body 12, preferably through a pedicle, chain 200 may be inserted.

Figure 9C:
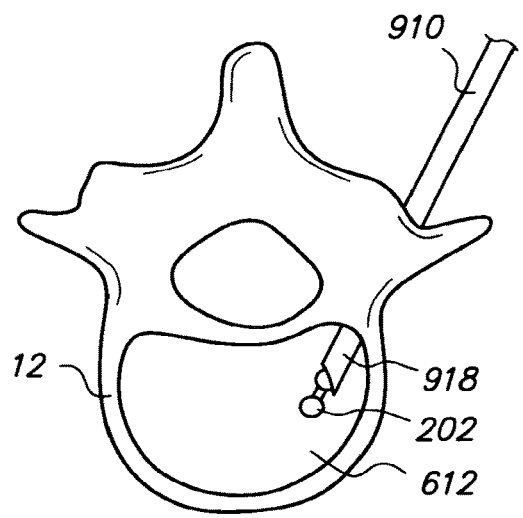
Figure 9D:
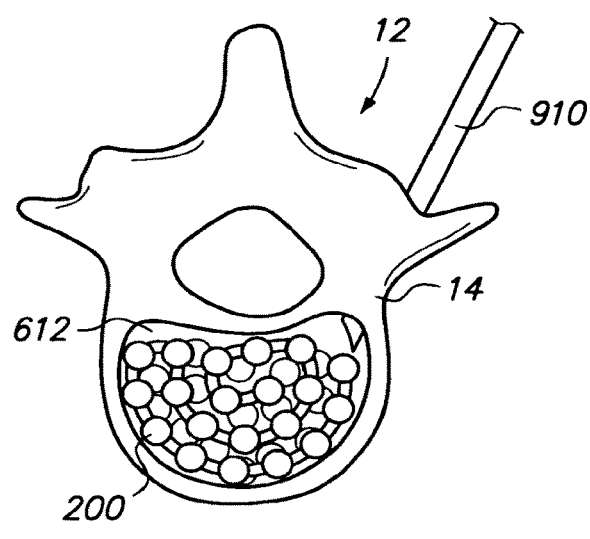

FIG. 9C shows first end 202 of a chain 200 being inserted through the introducer 910 into space 612 of vertebral body 12. Chain 200 may be forced into vertebral body 12, for example by manually applying an axial force from opposite end 204 of chain 200 to drive chain 200 through introducer 910. In other embodiments, a displacement member, sprocket, screw mechanism, or other device is used to apply an axial force for implanting chain 200, for example as described below with respect to FIGS. 11-13. In some embodiments, one long flexible monolithic device 200 may be inserted and impacted into the surgical site. Alternatively, multiple shorter or different chain devices 200 and/or other implants can be impacted or otherwise inserted into the desired cavity, void or space. The multiple shorter chain devices may be attached to each other sequentially end to end as they are inserted. In this manner as one chain is almost inserted, and with an end extending out of the patient, the leading end of the next chain is attached to the chain that is partially inserted. FIG. 9D shows the one or more chains 200 completely inserted into the central portion 612 of vertebral body 12.

Other suitable procedures and materials for inserting a cannula through which an FMC may be introduced are described, for example, in U.S. Provisional Patent Application No. 60/722,064, filed Sep. 28, 2005 entitled "Apparatus and Methods for Vertebral Augmentation using Linked Bodies", which is incorporated by reference herein in its entirety. A chain or other implant 200 may compact the cancellous and/or osteoporotic bone inside a collapsed vertebral body during insertion into the vertebral body. Alternatively, a tool such as, for example, curettes or balloon catheter may be used to compress and compact the bone inside the vertebral body to create a cavity. The cavity in the vertebral body also may be formed by removing bone material as opposed to compacting the bone. For example, a reamer or other apparatus could be used to remove bone material from the inside of the vertebral body.

In other embodiments, PMMA or another bone cement or filler (for example bone chips or material collected from reaming the bone) may be inserted into vertebral body 12, e.g., through the introducer 910 or another cannula, sheath, syringe or other introducer, simultaneously with implant 200 to further enhance fixation or repair of a damaged region. Alternatively, the PMMA, bone cement or filler may be inserted into the interior of the bone after the chains (or portions thereof) have been inserted into the interior of the bone. Alternatively a bone growth promoting filler may be inserted into the vertebral body, and a plug of bone cement may be utilized to hold the implant 200 and filler material in the vertebrae 12. In this manner, the plug of cement is not inserted into the interior of the bone, but covers the opening created in the bone to insert the implant.

Figure 10A:
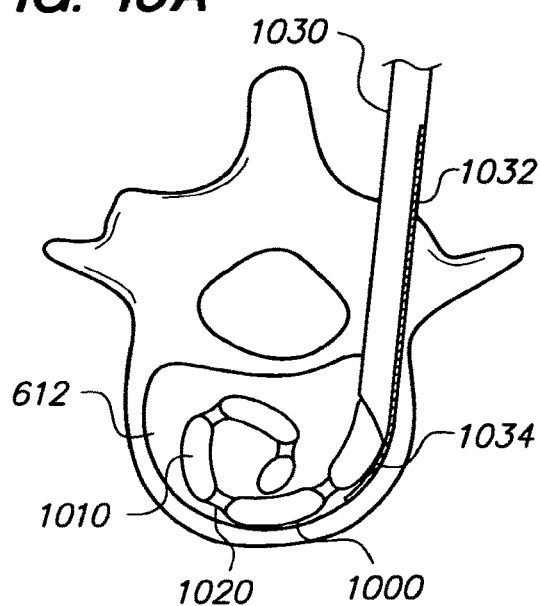
FIG. 10A is a cross-sectional top view of another method of implanting a flexible monolithic chain within a vertebral body.
Figure 10B:
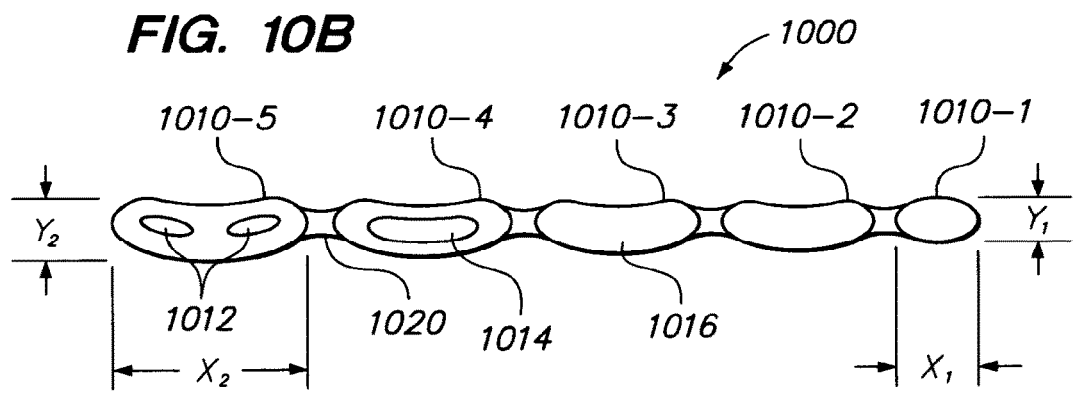
FIG. 10B is a top view of a flexible monolithic chain that may be used in the method of FIG. 10A.
Figure 10C:
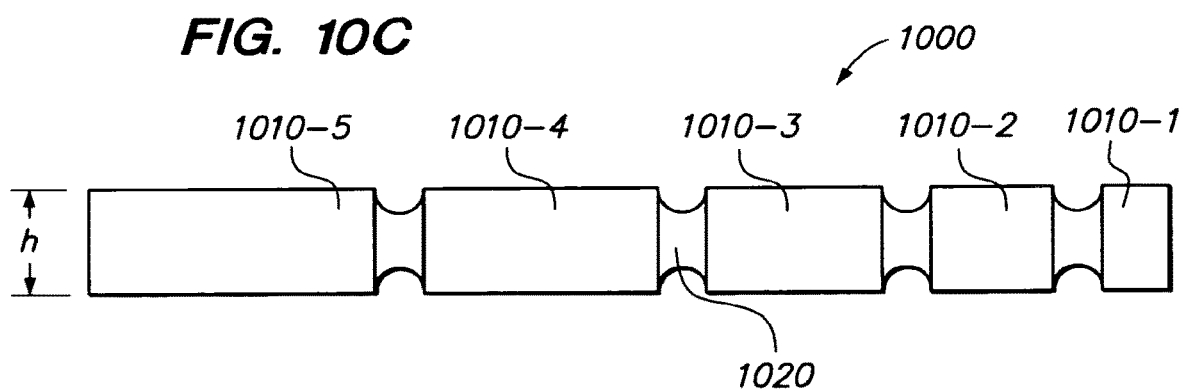
FIG. 10C is a side view of another embodiment of a flexible monolithic chain that may be used in the method of FIG. 10A.

A minimally invasive system for fusion or non-fusion implants and insertion instruments is shown in FIGS. 10A-C. As described above, a flexible monolithic chain device 1000 device may be inserted into a vertebral body 12, e.g., through a cannula 1030 or other introducer inserted through a pedicle 14 as shown in FIG. 10A. Optionally, a guide or other tool 1032 having a curved or otherwise configured tip 1034 may also be inserted through the cannula 1030 and serve to distract the end plates of the vertebral body 12 and/or guide the bodies 1010 of chain 1000 in a desired direction. As chain 1000 is forced into vertebral body 12, flexible portions 1020 of chain 1000 may bend or flex to allow chain 1000 to curve or otherwise convolute in a desired fashion to fill the central portion 612. The flexible portions allow the implant to fold and collapse upon itself to substantially fill the interior of the bone preferably with minimal porosity or open spaces.

As shown in FIG. 10B, chain 1000 may have flexible portions, or struts, 1020 and non-flexible portions 1010 of different shapes. For example, flexible joints 1010 may be narrower than the non-flexible portions 1020, which may be kidney shaped, rectangular, or any other shape. Some of the non-flexible bodies may be a different size or shape than others, for example they may increase in size from a first non-flexible body 1010-1 having a width $Y_1$ to a last non-flexible body 1010-5 having a width $Y_2$ that is larger than width $Y_1$. For example, in the exemplary embodiment of FIG. 10B, width Y1 may be between about 5 mm and about 2 mm or less, and width Y2 may be between about 6 mm and about 8 mm or less. Similarly, body 1010-1 may have a length $X_1$ that is substantially shorter than the length $X_2$ of body 1010-5. For example, in the exemplary embodiment of FIG. 10B, length $X_1$ may be between about 2 mm and about 6 mm, and length $X_2$ may be between about 6 mm and about 14 mm. Overall length of chain 1000 may vary depending upon the desired application, for example from about 10 mm to about 150 mm, more preferably from about 40 mm to about 100 mm. Of course various other sizes and relative differences in size or configuration of width, circumference, shape, curvature, or other dimensions of bodies 1010 and/or flexible portions 1020 may be employed without departing from the scope of the present invention.

In some embodiments, one or more of the bodies 1010 may have one or more openings or cavities 1012 or 1014. Such openings or cavities 1012, 1014 may be empty or may be filled, for example with a cement, bone filler, adhesive, graft material, therapeutic agent, or any other desired materials. In other embodiments, an implant device 1000 may be coated with different substances that will support and promote bone healing, reduce infections and/or deliver therapeutic agents to the treated site. Additionally, the non-flexible or flexible portions may also have porous surfaces 1016, for example to facilitate in growth of bone or other tissues.

FIG. 10C shows another embodiment of a chain 1050, having substantially rectangular or cylindrical bodies 1010-1, 1010-2, 1010-3, 1010-4 and 1010-5, which may be separated by flexible link portions 1020, and may have the same or different dimensions as each other. In FIG. 10C all of the bodies 1010-1, 1010-2, 1010-3, 1010-4 and 1010-5 have the same height h but different lengths. The struts 1020 in FIG. 10C have a different smaller height than the bodies 1010.

FIG. 11 is a side view illustration of an insertion device 1100 for implanting a chain 200 into a bone or other desired structure. For example, insertion device 110 may include an insertion tube or cannula 1120 having a wall 1122 and a lumen 1223. Disposed within and extending through at least a portion of lumen 1223 is a rotatable screw mechanism 1110 having spiral threads 1114 surrounding an axial shaft 1112. Threads 1114 preferably extend from shaft and are dimensioned and spaced to engage chain 200, e.g., between bodies 210. When screw 1110 is rotated, e.g., by turning a handle 1130, the threads 1114 engage bodies 210 and force chain 200 axially through the lumen 1223 of the cannula and into the desired bone or other region. Such an insertion device may allow for enhanced insertion force of an implant, for example in order to move vertebral endplates to restore the height of the end plates of a vertebra, to compress cancellous bone in a region of the implant, or to otherwise force the implant into a desired area.

FIGS. 12 and 13 show other mechanisms for forcing a chain 200 through an introducer and into a desired region. In particular, FIG. 12 shows a plunger, pusher or other displacement member 1200 inserted within cannula 1102. Displacement member 1200 may be used to displace or push bodies 210 of chain through cannula 1102 and into vertebral body 12. Displacement member 1200 may be driven, for example, by pressure, e.g., from a syringe, rod, or other apparatus that forces displacement member 1200 into cannula 1102 and towards vertebral body 12. In the embodiment of FIG. 13, a sprocket 1300 or apparatus that may be wheel-like and have teeth, gears or other extensions 1302 may be configured to engage bodies 210 of chain 200. Sprocket 1300 rotates about a central axis 1304, for example in a direction shown by arrow 1306, teeth 1302 may engage bodies 210 and force chain 200 through cannula 1102 and into portion 612 of vertebral body 12. In other embodiments, sprocket 1300 may be rotated in an opposite direction to remove some or all of chain 200, for example after restoring a height of vertebral body 12.

The flexible monolithic chain devices and/or methods described herein may be used in conjunction with or instead of other methods or devices for augmenting vertebral bodies or other bones, such as, for example are described in U.S. Provisional Patent Application No. 60/722,064, filed Sep. 28, 2005 entitled "Apparatus and Methods for Vertebral Augmentation using Linked Bodies", which is incorporated by reference herein in its entirety.

Figure 14A:
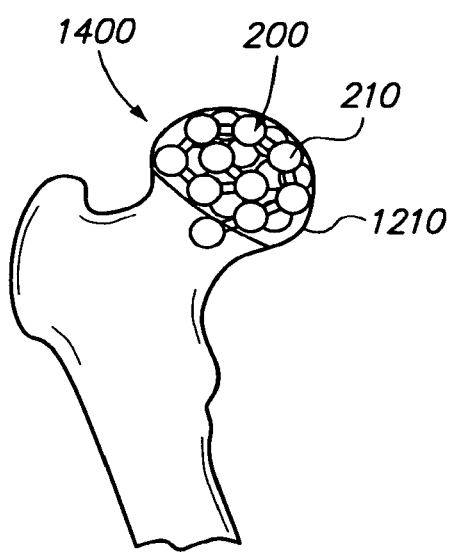
FIGS. 14A and B are cross-sectional side views of a flexible monolithic chain implanted into the head of a femur.
Figure 14B:
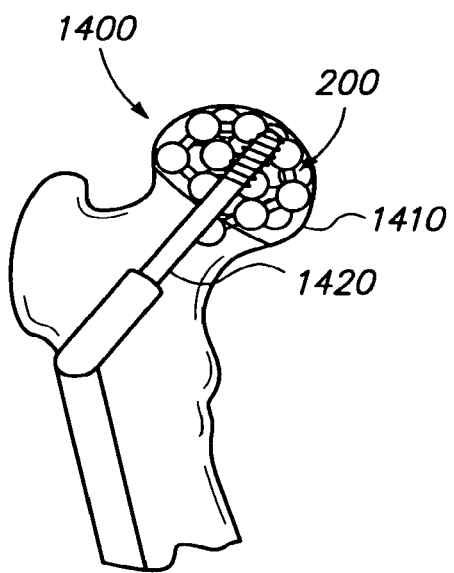
Figure 15:
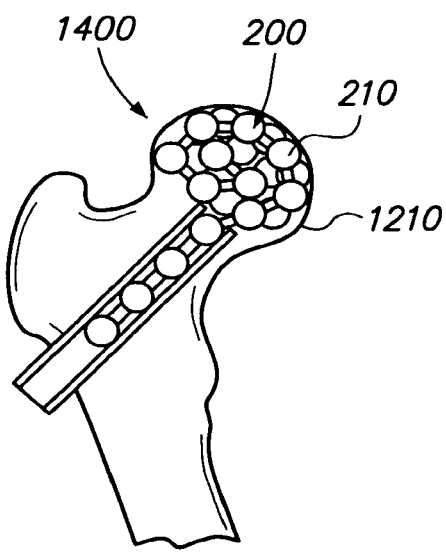
FIG. 15 is a cross-sectional view of a chain implant inserted through a cannula into the head of a femur.

Although the apparatus and methods described herein thus far have been described in the context of repositioning and augmenting vertebrae for example in the context of vertebral compression fractures and deformations in spinal curvature, various other uses and methods are envisioned. For example, in some embodiments, an implantable monolithic chain 200 may be used to augment vertebrae where a compression or a compression fracture has not yet occurred and thus can be preventative in nature. Also, in some embodiments the chain can be used in-between two vertebra. For example, the chain implant can be inserted in the annulus of a spinal disc, or the disc can be removed and the chain implant inserted in-between adjacent vertebra to promote fusion of adjacent vertebrae. The chain implant in some embodiments may be insertable in an additional implant, such as a cage implanted in-between adjacent vertebrae. The chain implant may also be used to reposition and/or augment other damaged bone regions such as a fractured or weakened proximal femur 1400 as shown in FIG. 14. In such embodiments, for example, one or more chains 200 may be inserted into a head 1410 of femur 1400, e.g., through a cannula 1102 or other introducer as show in FIG. 15. Once inserted, chain 200 may compact material within head 1410 and provide solid support to augment the head 1410. A bone cement or other filler may also be used to aid augmentation. In other embodiments, another implant 1420 may be inserted in addition to or instead of one or more chains 200.

In some embodiments, the implants and methods described herein may be used in conjunction with other apparatus and methods to restore lordosis and augment the vertebral body. For example, one or more chains 200 may be used in conjunction with known procedures, e.g., a balloon kyphoplasty, that may be used to begin repositioning of a vertebral body and/or create a space within the body for chain 200. In other embodiments, one or more chains 200 may be used in conjunction with other tools or external fixation apparatus for helping to manipulate or fix the vertebrae or other bones in a desired position.

In another embodiment, a kit comprises various combinations of assemblies and components. A kit may include, for example, a cannula or other introducer and one or more flexible monolithic chains 200. The one or more chains 200 may be provided in different sizes, e.g., different lengths and/or diameters. In other embodiments, a kit may include an introducer, one or more chains, and a syringe or other apparatus for injecting a cement or other filler into a vertebral body or other space. In other embodiments, a kit may comprise one or more balloon catheters, curettes, and other instruments and may additionally include anchoring elements, tensioning members, fixation members, or any combination thereof, for example as described in U.S. Provisional Patent Application No. 60/722,064, entitled "Apparatus and Method for Vertebral Augmentation using Linked Bodies", filed Sep. 28, 2005, which is incorporated by reference herein in its entirety. One skilled in the art will appreciate that various other combinations of devices, components and assemblies can be made and are intended to fall within the scope of the present invention.

In other embodiments, various minimally invasive implants and methods for alleviating discomfort associated with the spinal column may employ anchors and other implants described herein. For example, a monolithic chain implant within an expandable container (not shown), may be implanted between spinous processes of adjacent vertebrae to distract the processes and alleviate pain and other problems caused for example by spinal stenosis, facet arthropathy, and the like. For example, augmentation systems described herein may be used instead of or in addition to expandable interspinous process apparatus and methods described in U.S. Patent Publication number 2004/018128 and U.S. Pat. No. 6,419,676 to Zucherman et al. For example, a cannula may be inserted laterally between adjacent spinous processes to insert a container that may be filled with the flexible chains and expand the container and thus keep the adjacent spinous processes at the desired distance. Alternatively, a balloon container, with a deflatable balloon portion can be inserted laterally through adjacent spinous processes and filled with the flexible chains to expand the balloon to a desired size to hold adjacent spinous processes at a desired distances. The balloon can thereafter be sealed and detached from the catheter. Other materials may be inserted within the balloon volume to supplement flexible bodies.

While the foregoing description and drawings represent the preferred embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. The presently disclosed embodiments are therefore to be considered in all respects as illustrative and not restrictive, the scope of the invention being indicated by the appended claims, and not limited to the foregoing description.

What is claimed is:

1. An apparatus for augmentation of body tissues comprising:
   a flexible elongated member having a longitudinal length substantially larger than its height or its width, the flexible elongated member being formed as an integral monolithic elongated member, wherein the member comprises:
      a plurality of bodies, the bodies having a first cross-sectional size;
      a plurality of links interconnecting the bodies, the bodies and links connected end-to-end to form the elongated member, the links having a second cross-sectional size, the first cross-sectional size being larger than the second cross-sectional size; the elongated member being formed of bone, wherein the links are demineralized through their entire thickness and the bodies are partially demineralized across the entire outer surface thereof; and
      a therapeutic agent adsorbed, sorbed or perfused onto or into the elongated member;
   wherein the member has at least one link configured to transition between a first state, where the link is sufficiently rigid to prevent contact between two bodies connected thereto, and a second state, where the link is sufficiently flexible to allow contact between the two bodies connected thereto;
   wherein a moisture content of the at least one link is greater in the second state than in the first state.

2. The apparatus according to claim 1 wherein the flexible elongated monolithic member exhibits osteoconductive, osteoinductive or osteogenic properties.

3. The apparatus according to claim 2 wherein the therapeutic agent is selected from the group consisting of drug agents, biologics, bone morphogenic proteins, tissue growth enhancing agents, bone cements, antibiotics and bone growth stimulating substances.

4. An apparatus for augmentation of body tissues comprising:
   a flexible elongated member having a longitudinal length substantially larger than its height or its width, the flexible elongated member being formed as an integral monolithic elongated member, wherein the member comprises:
      a plurality of bodies, the bodies having a first cross-sectional size;
      a plurality of links interconnecting the bodies, the bodies and links connected end-to-end to form the elongated member, the links having a second cross-sectional size, the first cross-sectional size being larger than the second cross-sectional size; the elongated member being formed of bone, wherein the links are demineralized through their entire thickness and the bodies are partially demineralized across the entire outer surface thereof; and
      a coating on at least a portion of the flexible elongated member, the coating comprising a therapeutic agent, a bone cement, an antibiotic, a bone growth stimulating substance, a bone morphogenic protein, a drug agent or a biologic, or any combination thereof
   wherein the member has at least one link configured to transition between a first state, where the link is sufficiently rigid to prevent contact between two bodies connected thereto, and a second state, where the link is sufficiently flexible to allow contact between the two bodies connected thereto;
   wherein a moisture content of the at least one link is greater in the second state than in the first state.

5. An apparatus for augmentation of body tissues comprising:
   a flexible elongated member having a longitudinal length substantially larger than its height or its width, the flexible elongated member being formed as an integral monolithic elongated member, wherein the member comprises:
a plurality of bodies, the bodies having a first cross-sectional size;
a plurality of links interconnecting the bodies, the bodies and links connected end-to-end to form the elongated member, the links having a second cross-sectional size, the first cross-sectional size being larger than the second cross-sectional size; the elongated member being formed of bone, wherein the links are demineralized through their entire thickness and the bodies are partially demineralized across the entire outer surface thereof;
wherein at least one of the bodies is formed with at least one through bore, cavity, recess or depression in the outer surface; and
wherein the member has at least one link configured to transition between a first state, where the link is sufficiently rigid to prevent contact between two bodies connected thereto, and a second state, where the link is sufficiently flexible to allow contact between the two bodies connected thereto;
wherein a moisture content of the at least one link is greater in the second state than in the first state.

6. The apparatus according to claim 5 where the bone is allograft bone.

7. The apparatus according to claim 6 wherein the allograft bone is cortical bone.

8. The apparatus according to claim 7 wherein the bore, cavity, recess or depression contains a cement, a bone filler, an adhesive, a graft material, a drug agent, a bone morphogenic protein, a tissue growth enhancing agent, and/or an osteoinductive agent or any combination thereof.

9. The apparatus according to claim 7 wherein the bore, cavity, recess or depression contains bone chips, bone particulates, bone fibers, or combinations thereof.

10. The apparatus according to claim 9 wherein the bore, cavity, recess or depression also contains a tissue growth enhancing agent.

11. The apparatus according to claim 10 wherein the bone chips, bone particulates, or bone fibers are partially or fully demineralized.

12. The apparatus according to claim 9 wherein the bone chips are partially or fully demineralized.

\* \* \* \* \*